United States Patent
Shoichet et al.

(10) Patent No.: US 6,531,558 B1
(45) Date of Patent: Mar. 11, 2003

(54) FLUOROMONOMERS AND METHOD OF PRODUCTION, AND NEW FLUOROPOLYMERS PRODUCED THEREFROM

(76) Inventors: Molly S. Shoichet, 15 Austin Crescent, Toronto, Ontario (CA), M5R 3E4; Robert D. Lousenberg, 501-35 Charles Street, Toronto Ontario (CA), M4Y 1R6

(*) Notice: Subject to any disclaimer, the term of this patent is extended or adjusted under 35 U.S.C. 154(b) by 0 days.

(21) Appl. No.: 09/274,960

(22) Filed: Mar. 23, 1999

Related U.S. Application Data
(60) Provisional application No. 60/080,144, filed on Mar. 31, 1988.

(30) Foreign Application Priority Data

Oct. 30, 1998 (CA) .............................................. 2252298

(51) Int. Cl.$^7$ ................................................. C08F 16/24
(52) U.S. Cl. ........................................................ 526/247
(58) Field of Search ......................................... 526/247

(56) References Cited

U.S. PATENT DOCUMENTS

| | | | |
|---|---|---|---|
| 2,917,548 A | 12/1959 | Dixon | |
| 3,277,068 A | 10/1966 | Wall et al. | |
| 5,162,468 A | 11/1992 | Babb et al. | |
| 5,198,513 A | 3/1993 | Clement et al. | |

OTHER PUBLICATIONS

Feiring et al., "Synthesis of Arylperfluoroalkyl Ethers by Direct Fluorination", Journal of Fluorine Chemistry, No. 89, pp. 31–34, Elsevier Science S.A. 1998.
Okuhara et al., "Preparation and Properties of Alkyl Trifluorovinyl Ethers and Related Compounds", vol. 35, No. 4, pp. 532–535.

*Primary Examiner*—Edward J. Cain
(74) *Attorney, Agent, or Firm*—Lynn C. Schumacher; Will & Schumacher

(57) ABSTRACT

The present invention provides new fluoromonomers having the generic structure: $CF_2=CF(OCH_2CH_2)_nOR$ where n is an integer and R is a functional group and methods for producing same. A new method of synthesizing the fluoromonomers is provided. The present invention also relates to new fluoropolymers prepared from any one or combination of the new fluoromonomers and having the generic structure: $-[-CF_2CF\{(OCH_2CH_2)_nOR\}-]_m-$ where n is an integer, m is an integer and R represents an unsubstituted or inertly substituted hydrocarbyl group. The method also relates to new copolymers or terpolymers prepared from the new fluoromonomers alone, the new fluoromonomers and existing fluoromonomers or the new fluoromonomers and existing hydrocarbon or functionalized hydrocarbon monomers.

33 Claims, 6 Drawing Sheets

FLUOROMONOMERS AND METHOD OF PRODUCTION, AND NEW FLUOROPOLYMERS PRODUCED THEREFROM

CROSS REFERENCE TO RELATED U.S. APPLICATION

This application relates to U.S. Provisional patent application, Ser. No. 60/080,144, filed on Mar. 31, 1998, entitled NEW FLUOROMONOMERS AND METHODS OF PRODUCTION, AND NEW FLUOROPOLYMERS PRODUCED THEREFROM.

FIELD OF THE INVENTION

The present invention relates to new fluoromonomers having the generic structure: $CF_2=CF(OCH_2CH_2)_nOR$ where n is an integer and R is a functional group and methods for producing same. The present invention also relates to new fluoropolymers prepared from any one or combination of the new fluoromonomers and having the generic structure: $-[-CF_2CF\{(OCH_2CH_2)_nOR\}-]_m-$ where n is an integer, m is an integer and R are any one or combination of functional groups. The method also relates to new copolymers or terpolymers prepared from the new fluoromonomers alone, the new fluoromonomers and existing fluoromonomers or the new fluoromonomers and existing hydrocarbon monomers.

BACKGROUND OF THE INVENTION

Fluoromonomers 1-alkoxy/aryloxy-1,2,2-trifluoroethenes or 1-(substituted) fluoro/perfluoroalkoxy-1,2,2-trifluoroethenes(trifluorovinyl ethers or TFVEs) have been previously synthesized by two principal synthetic routes that do not involve the use of elemental halogens or hydrogen fluoride.

For example, U.S. Pat. No. 2,917,548 to Dixon [1] discloses the preparation and polymerization of 1-methoxy-1,2,2-trifluoroethene which was prepared by the reaction of sodium methoxide with tetrafluoroethylene. This reaction was expanded by Okuhara, et al. *Bull. Chem. Soc. Jap.* 1962, 35, 532–535 [2] to include ethoxide, isopropoxide and tert-butoxide substituted TFVEs. 1-ethoxy-1,2,2-trifluoroethene was polymerized with "common free radical initiators". This method required high pressure reaction equipment to achieve high tetrafluoroethylene pressures and long reaction times (and in one instance an explosion was reported) [2].

U.S. Pat. No. 3,277,068 to Wall et al. [3] discloses the preparation of 1-phenoxy-1,2,2-trifluoroethenes, and polymers derived therefrom. The monomer was prepared by the reaction of an alkali metal phenoxide with tetrafluoroethylene. Tetrafluoroethylene pressures greater 200 PSI were required. No phase transfer catalyst was used.

U.S. Pat. No. 5,162,468 to Babb et al. [4] and U.S. Pat. No. 5,198,513 to Clement et al. [5] disclose the preparation and polymerization of trifluorovinyl compounds, $CF_2=CF-O-R-(O-CF=CF_2)_m$, where R represents an unsubstituted or inertly substituted hydrocarbyl group and m is an integer of from 1 to 3. These compounds were prepared by reaction of an appropriate salt with 1,2-dihalo-1,1,2,2-tetrafluoroethane to form intermediates, $Z-CF_2CF_2-O-R-(O-CF_2CF_2-Z)_m$, where each Z is independently iodine or bromine. Elimination of the halogen atoms represented by Z formed the trifluorovinyl compounds.

U.S. Pat. No. 3,114,778 to Fritz et al. [6], U.S. Pat. No. 3,180,895 to Harris et al. [7], and U.S. Pat. No. 3,250,808 to Moore et al. [8] disclose a method to prepare 1-fluoro/perfluoroalkoxy-1,2,2-trifluoroethenes, and polymers derived therefrom. These monomers where prepared by pyrolysis of 2-fluoro/perfluoroalkoxy-2,3,3,3-tetrafluoropropionic acid intermediates or derivatives thereof. U.S. Pat. No. 5,391,796 to Farnham [9] discloses a method to prepare 1-(substituted)fluoro/perfluoroalkoxy-1,2,2-trifluoroethenes, and polymers derived therefrom. These monomers were prepared by pyrolysis of compounds represented by $R^1-O-(C_2F_4)CO_2SiR^2_3$, where $R^1$ represents an unsubstituted or inertly substituted hydrocarbyl or fluorocarbyl group and $R^2$ is independently hydrocarbyl, substituted hydrocarbyl or an oxysilyl group.

Pellerite *J. Fluorine Chem.* 1990, 49, 43–46 [10] reported the synthesis of 1-alkoxy-1,2,2-trifluoreoethenes by pyrolysis of 2-alkoxy-2,3,3,3-tetrafluoropropionate salts. The pyrolysis resulted in unanticipated chemistry with negligible to low yields of 1,2,2-trifluoroethenes depending on the alkoxy substituent and propionate counterion.

U.S. Pat. No. 4,337,221 [11] and U.S. Pat. No. 4,515,989 to Ezzell et al. [12] disclose the preparation 1-(substituted) fluoro/perfluoroalkoxy-1,2,2-trifluoroethenes and polymers derived therefrom. The former were prepared from 2-fluoro/perfluoroalkoxy-3-chloro-2,3,3-trifluoropropionyl fluoride intermediates. The intermediates reacted with sodium carbonate at temperatures between ambient and 80° C. to form the monomers in very high yields.

Fluoropolymers

Fluorochemicals are hydrophobic, oleophobic and have extremely low surface energies, making them useful blooming agents in processing applications [13]. Fluoropolymers are chemically inert having unique properties of thermal stability and biological acceptability. Consequently, they have been used in numerous applications, from chemical erosion resistant devices to coatings and linings in chemical storage tanks to vascular grafts [13]. Commercial fluoropolymers have been used as coatings and include, for example: (1) a block terpolymer of 65% vinylidene fluoride, 25% tetrafluoroethylene and 10% vinyl ester (e.g. vinyl butyrate) which can be cured by UV-irradiation; (2) tetrafluoroethylene-hydroxyalkyl vinyl ether copolymer which is used in acrylic sheets; (3) fluoroolefin-vinyl ether copolymers, Lumiflon® comprises alternating sequences of fluoroolefin and several specific vinyl monomer units.

Fluoropolymers, such as poly(tetrafluoroethylene) or poly(tetrafluoroethylene-co-hexafluoropropylene), are difficult to process, insoluble in common organic solvents and chemically inert, requiring highly reactive species for surface modification [14]. Perfluorinated ether groups on trifluorovinyl ethers (TFVEs) have been shown to improve the processability of the resulting polymer [15]. Incorporating a hydrocarbon ether group into the fluoromonomer will likely further improve the processability of the resulting polymers; however no one has yet synthesized (or polymerized) the hydrocarbon TFVEs described herein. The hydrocarbon ether group is anticipated to improve the solubility of the resulting poly(TFVE)s in common organic solvents, thereby further expanding the range of applications.

SUMMARY OF THE INVENTION

It is an object of the present invention to provide new fluoromonomers, a method for their production and fluoropolymers produced from the fluoromonomers.

The present invention provides new fluoromonomers having the generic structure: $CF_2=CF(OCH_2CH_2)_nOR$ where n is an integer and R represents an unsubstituted or inertly substituted hydrocarbyl group. A new method of synthesizing the fluoromonomers is provided. The present invention also relates to new fluoropolymers prepared from any one or combination of the new fluoromonomers and having the generic structure: —[—$CF_2CF\{(OCH_2CH_2)_nOR\}$—]$_m$— where n is an integer, m is an integer and R represents an unsubstituted or inertly substituted hydrocarbyl group. The method also relates to new copolymers or terpolymers prepared from the new fluoromonomers alone, the new fluoromonomers and existing fluoromonomers or the new fluoromonomers and existing hydrocarbon monomers.

The present invention provides a fluoromonomer of the following general formula (I), comprising;

$$CF_2=CF(OCH_2CH_2)_nOR \quad (I)$$

wherein n is an integer greater than or equal to 1 and wherein R represents an unsubstituted or inertly substituted hydrocarbyl group.

The invention also provides a process for synthesis of a fluoromonomer having the following general formula (I), $$CF_2=CF(OCH_2CH_2)_nOR \quad (I)$$

wherein n is an integer, and wherein R represents an unsubstituted or inertly substituted hydrocarbyl group, comprising the steps of:

providing an effective alkali metal alkoxide;

mixing tetrafluoroethylene with said alkali metal alkoxide in the presence of an effective phase transfer catalyst at an effective temperature to form a mixture, the phase transfer catalyst being selected from the group consisting of crown ethers and tetraalkylammonium salts; and isolating the fluoromonomer from the mixture.

The invention also provides a fluoropolymer of the following general formula (II), comprising $$—[CF_2CF\{(OCH_2CH_2)_nOR\}]_m— \quad (II)$$

wherein n is an integer, m is an integer, and wherein R represents an unsubstituted or inertly substituted hydrocarbyl group.

The invention provides copolymers comprising a first fluoromonomer of the general formula $CF_2=CF(OCH_2CH_2)_nOR$, wherein n is an integer, and wherein R represents an unsubstituted or inertly substituted hydrocarbyl group, and a second monomer of the general formula $CF_2CXY$ wherein X and Y are selected from the group consisting of hydrogen, halogen, hydrocarbyl groups, inertly substituted hydrocarbyl groups and any combination thereof. Alternatively, the second monomer may be a second fluoromonomer of the general formula CFXCYZ, wherein n is an integer, wherein R represents an unsubstituted or inertly substituted hydrocarbyl group, and wherein X, Y and Z are selected from the group consisting of hydrogen, halogens, unsubstituted hydrocarbyl and inertly substituted hydrocarbyl groups and any combination thereof. Alternatively, the second monomer may have a generic formula CXYCAB wherein X, Y, A, B are selected from the group consisting of hydrogen, halogen, unsubstituted hydrocarbyl groups, inertly substituted hydrocarbyl groups and any combination thereof.

The present invention provides a fluoromonomer of the following general formula $CGJ=CL(OCH_2OCH_2)_nOR$ wherein n is an integer, and wherein R represents an unsubstituted or inertly substituted hydrocarbyl group. G and J are selected from the group consisting of chlorine, fluorine, trifluoromethyl and hydrogen, and wherein L is selected from the group consisting of chlorine, fluorine and hydrogen, and wherein at least one of G, J and L is fluorine.

The present invention provides a fluoropolymer of the following general formula, comprising —[CGJCL{$(OCH_2CH_2)_nOR$}]$_m$—, wherein n is an integer, m is an integer and R represents an unsubstituted or inertly substituted hydrocarbyl group, and wherein G and J are selected from the group consisting of chlorine, fluorine, trifluoromethyl and hydrogen, and wherein L is selected from the group consisting of chlorine, fluorine and hydrogen, and wherein at least one of G, J and L is fluorine.

Copolymers are provided comprising a fluoromonomer of the general formula $CGJ=CL(OCH_2CH_2)_nOR$, wherein G and J are selected from the group consisting of chlorine, fluorine, trifluoromethyl and hydrogen, and wherein L is selected from the group consisting of chlorine, fluorine and hydrogen, and wherein at least one of G, J and L is fluorine. The copolymers may be produced using a second fluoromonomer of the general formula $CF_2CXY$, wherein n is an integer and R represents an unsubstituted or inertly substituted hydrocarbyl group, and wherein X and Y are selected from the group consisting of hydrogen, halogens, unsubstituted hydrocarbyl groups, inertly substituted hydrocarbyl groups and any combination thereof. Alternatively, the second monomer may be of the general formula CFXCYZ, wherein X, Y and Z are selected from the group consisting of hydrogen, halogens, hydrocarbyl groups, inertly substituted hydrocarbyl groups and any combination thereof. Or, alternatively the second monomer may have a generic formula CXYCAB, wherein X, Y, A, B are selected from the group consisting of hydrogen, halogen, unsubstituted hydrocarbyl groups, inertly substituted hydrocarbyl groups and any combination thereof.

The invention also provides a terpolymer comprising a first fluoromonomer of the following general formula $$CF_2=CF(OCH_2CH_2)_nOR$$

wherein n is an integer greater than or equal to 1 and R represents an unsubstituted or inertly substituted hydrocarbyl group, and a second fluoromonomer of the following general formula $$CF_2=CF(OCH_2CH_2)_nOR'$$

wherein n is an integer greater than or equal to 1 and R' represents an unsubstituted or inertly substituted hydrocarbyl group, wherein R and R' are different. The terpolymer includes a third fluoromonomer which may have the general formula 1) $CF_2CXY$, wherein X and Y are selected from the group consisting of hydrogen, halogen, unsubstituted hydrocarbyl groups, inertly substituted hydrocarbyl groups and any combination thereof; or 2) a fluoromonomer of the general formula CFXCYZ, wherein X, Y and Z are selected from the group consisting of hydrogen, halogen, unsubstituted hydrocarbyl and inertly substituted hydrocarbyl groups and any combination thereof; or 3) a monomer having a generic formula CXYCAB, wherein X, Y, A, B are selected from the group consisting of hydrogen, halogen, unsubstituted hydrocarbyl groups, inertly substituted hydrocarbyl groups and any combination thereof; or 4) a fluoromonomer of the following general formula $$CF_2=CF(OCH_2CH_2)_nOR''$$

wherein n is an integer greater than or equal to 1 and R'' represents an unsubstituted or inertly substituted hydrocarbyl group, wherein R, R' and R'' are different from each other.

The present invention provides a graft copolymer comprising a polymer graft and a polymer backbone, the backbone comprising a polymer selected from the group consisting of polystyrene, polyurethane, polyester, polyether, polyethylene, polypropylene, poly(carbonate), poly(anhydride), poly(vinyl chloride), poly(acrylonitrile), poly($\alpha$-hydroxyesters), poly(tetrafluoroethylene), poly(vinylidene fluoride), poly(chlorotrifluoroethylene), nylon, poly(ethylene terephthalate), poly(amide), poly(amine), poly(amino acid), poly(arylate), poly(acrylate), poly(acetate) and any combination thereof; and the polymer graft comprising a fluoropolymer of the following general formula —[CF$_2$CF{(OCH$_2$CH$_2$)$_n$OR}]$_m$— wherein n is an integer, m is an integer and R represents an unsubstituted or inertly substituted hydrocarbyl group.

The present invention provides a fluoropolymer blend comprising a fluoromonomer of the following general formula CF$_2$=CF(OCH$_2$CH$_2$)$_n$OR wherein n is an integer greater than or equal to 1 and R represents an unsubstituted or inertly substituted hydrocarbyl group; and a polymer selected from the group consisting of polystyrene, polyurethane, polyester, polyether, polyethylene, polypropylene, poly(carbonate), poly(anhydride), poly(vinyl chloride), poly(acrylonitrile), poly($\alpha$-hydroxyesters), poly(tetrafluoroethylene), poly(vinylidene fluoride), poly(chlorotrifluoroethylene), nylon, poly(ethylene terephthalate), poly(amide), poly(amine), poly(amino acid), poly(acrylate), poly(acetate) and any combination thereof.

The fluoropolymer blends may also be produced using the fluoropolymer of the following general formula —[CF$_2$CF{(OCH$_2$CH$_2$)$_n$OR}]$_m$— wherein n is an integer, m is an integer and R represents an unsubstituted or inertly substituted hydrocarbyl group and the polymers listed above.

In another aspect of the invention there is provided biologically useful materials exhibiting low protein absorption comprising fluoropolymers blended with biologically acceptable polymer, the fluoropolymers being selected from the group consisting of —[CF$_2$CF{(OCH$_2$CH$_2$)$_n$OR}]$_m$—, wherein n is an integer, m is an integer and R represents an unsubstituted or inertly substituted hydrocarbyl group.

BRIEF DESCRIPTION OF THE DRAWINGS

The present invention will now be described, by way of example only, reference being had to the accompanying drawings, in which.

DETAILED DESCRIPTION OF THE INVENTION

1-Alkoxy-1,2,2-trifluoroethene(trifluorovinyl ethers or TFVEs) monomers and polymers were prepared to overcome the limited processability and solubility of commercial fluoropolymers [15]. To further enhance interactions with other polymers in processing or blend applications, the inventors have prepared TFVEs with hydrocarbon oligoether pendant groups. Unlike the perfluorinated backbone, the pendant group is hydrophilic and can interact with other polymers via hydrogen-bonding. While sacrificing on chemical inertness, the greater solubility of these new TFVE polymers in common organic solvents broadens the number of potential applications.

New monomers, $CF_2=CF(OCH_2CH_2)_nOR$, where n is an integer and R is a functional group, i.e. an unsubstituted or inertly substituted hydrocarbyl group have been polymerized. "Hydrocarbyl" is a monovalent or divalent group containing only carbon and hydrogen. "Substituted hydrocarbyl" is a monovalent or divalent group containing only carbon and hydrogen which contains inert substituents. "Inert" in this context means that the substituents do not change or react chemically during the process and may include oxygen, nitrogen, sulfur, halogen, etc. functional groups.

Figure 1:
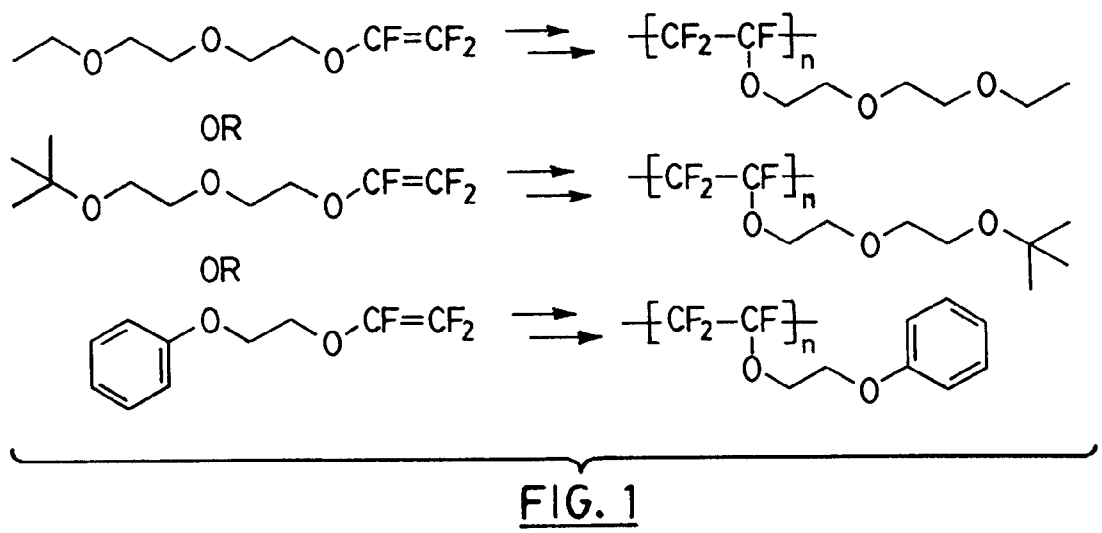
FIG. 1 illustrates three homopolymers prepared from the three monomers Et-TFVE, Bu-TFVE and Ph-TFVE.

Three new monomers, shown as the reactants in FIG. 1, have been polymerized: 1-[2-(2-ethoxyethoxy)ethoxy]-1,2, 2-trifluoroethene (Et-TFVE), 1-[2-(2-t-butoxyethoxy) ethoxy]-1,2,2-trifluoroethene (Bu-TFVE) and 1-(2-phenoxyethoxy)-1,1,2-trifluoroethene (Ph-TFVE). As shown in FIG. 1, the polymers have a fluorocarbon backbone and a hydrocarbon, oligoether pendant group, with a structure similar to that of poly(ethylene glycol) (PEG). The monomers have an ethylene glycol pendant group in common and different terminal functional groups. The presence of the oligoether group may render the fluoropolymer less protein adsorptive [16], thereby making it desirable for biomedical applications [17].

While the Et-TFVE has a pendant group structure similar to that of poly(ethylene glycol), the Bu-TFVE is a protected alcohol, which, upon de-protection, provides a reactive handle for further modification or crosslinking after polymerization. The Ph-TFVE provides a more rigid polymeric structure and may serve as a precursor to an ionic polymer. Unlike traditional perfluorinated polymers, such as poly (tetrafluoroethylene) or poly(tetrafluoroethylene-co-hexafluoropropylene) which require corrosive reagents for modification [18, 19], the hydroxyl functionality (shown as the protected t-butoxy group) incorporated into the pendant group of the backbone polymers of FIG. 1 facilitates modification.

For example, an acrylate group may be covalently attached to the hydroxyl group for applications in the paint formulation industry. In addition, the hydroxyl group provides a sight for crosslinking or in situ curing with polyisocyanates, for example (see Example 14 for more information). The poly(TFVE) can be used alone or as an additive in a blend. Blends of the poly(TFVE) with polystyrene have shown that the poly(TFVE) is surface active (see Example 15). For biomaterial applications, fluoropolymers have been found to be relatively biologically inert yet still adsorb proteins. The poly(TFVE)-polystyrene blend also demonstrates reduced protein adsorption relative to polystyrene films alone (see Example 16).

Synthesis of 1-alkoxy-1,2,2-trifluoroethenes (TFVEs)

Figure 2:
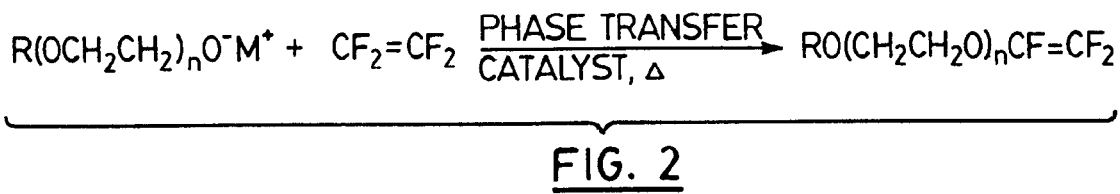
FIG. 2 shows the reaction for synthesis of the three novel fluoromonomers which are the reactants in FIG. 1.

FIG. 2 illustrates a new synthesis of TFVEs. The synthesis involves the reaction of tetrafluoroethylene (TFE) and an alkali metal alkoxide, $M^+O(CH_2CH_2O)_nR$, where M is an alkali metal cation, n is an integer and R is a functional group, i.e. an unsubstituted or inertly substituted hydrocarbyl group. "Hydrocarbyl" means a monovalent or divalent group containing only carbon and hydrogen. "Substituted hydrocarbyl" means a monovalent or divalent group containing only carbon and hydrogen which contains inert substituents. "Inert" in this context means that the substituents do not change or react chemically during the process.

The alkoxide is formed in situ in an inert solvent such as diethyl ether, glyme (preferred) or diglyme in the presence of a phase transfer catalyst such as crown ethers (18-crown-6 is preferred) or tetraalkylammonium salts. The alkoxide is formed by the reaction of the appropriate alcohol with a small molar excess of a strong base such as alkali metals or alkali metal hydrides (preferred). The formation of the alkoxide and reaction with TFE is carried out at elevated temperatures above ambient and less than 100° C. (preferably 65° C.). The reaction of the alkoxide with TFE is carried out in the presence of said phase transfer catalyst. The TFE pressure is maintained approximately constant at pressures between 50 and 100 PSI (preferably 60 PSI) for the duration of the reaction.

The improved synthesis has several advantages over the prior art (see Dixon [1], Okuhara [2], or Wall [3]). Firstly, preparation of the alkoxide in the presence of a phase transfer catalyst, which has not previously been reported, at elevated temperatures, more effectively converts the alcohol to the alkoxide. As a consequence, the amount of saturated ether byproduct, $HCF_2CF_2(OCH_2CH_2)_nOR$, is less than 1 mol % and there is no detectable residual alcohol. Phase transfer catalysts are known to increase alkoxide solubility by forming a complex with the alkali metal cation. Greater alkoxide solubility increases the rate of reaction and minimizes byproduct formation as evidenced by greater yields. Faster rates of reaction allow for TFE pressures less than 100 PSI to be used. TFE has been known to violently disproportionate at pressures above 100 PSI. Lower TFE pressures minimize the amount of excess TFE. Secondly, the oligoether portion, —$(OCH_2CH_2)_n$—, of said alkoxide further increases alkoxide solubility.

All TFVEs were characterized by gas chromatography (HP 9890) using a Restek Rtx-5 column (0.530×15 m with a 1.2 μm film thickness) with FID detector, helium carrier gas (35 cm/s) and a split ratio of ~25:1. A typical temperature profile held the initial temperature at 80° C. for 1 min, then ramped the temperature to 230° C. at 15° C./min, and finally held the temperature at 230° C. for 4 min.

$^1H$ and $^{19}F$ NMR spectra were taken at 300 and 282.2 MHz, respectively, on a Varian Gemini NMR spectrometer using TMS and $CFCl_3$ as external references and deuterated chloroform as the solvent.

EXAMPLE 1

Preparation of 1-(2-Phenoxy-ethoxy)-1,2,2-trifluoroethene (Ph-TFVE)

Ph-TFVE was prepared by mixing 3.38 g of NaH (0.141 mol) and 1 g of 18-crown-6 with 135 mL of glyme under inert atmosphere at 65° C. 15.0 g (0.109 mol) of 2-phenoxyethanol was slowly added to the flask and stirred at 65° C. for 1 h. The alkoxide was transferred to the dry 300 mL Parr reactor, stirred and heated at 65° C. for 1 h after which TFE gas was added. The pressure was maintained at ~50–60 PSI. A very slight exotherm (~5° C.) was initially observed. After 45 minutes, stirring was stopped and the reactor was cooled to room temperature. Excess TFE was carefully vented and the reactor contents transferred to a 500 mL Erlenmeyer flask. The mixture was diluted to 300 mL with pentane to effect complete precipitation of sodium salts. The mixture was filtered through a course frit funnel to remove sodium salts. The liquid fraction was rotary evaporated to give a clear yellow crude product. The crude product was vacuum fractionally distilled over potassium carbonate. 14.5 g (61% yield) of the desired product, 1-(2-phenoxy-ethoxy)-1,2,2-trifluoroethene, was isolated at a boiling point of 47–49° C. (pressure <0.3 mmHg, >99% purity by GC). $^{19}F$ NMR: δ=−122.9 (dd, 1F J=56, 103 Hz, CF), −129.6 (dd, 1F J=103, 108, CF), −135.1 (dd, 1F J=56, 108 Hz, CF); $^1H$ NMR: δ=7.3 (m, 2H, PhH), 6.95 (m, 3H, PhH), 4.3 (t, 2H, $CFOCH_2$), 4.2(t, 2H, $PhOCH_2$).

EXAMPLE 2

Preparation of 1-[2-(2-ethoxyethoxy)ethoxy]-1,2,2-trifluoroethene (Et-TFVE)

Et-TFVE was synthesized by mixing 3.22 g of NaH (0.134 mol) and 1 g of 18-crown-6 with 135 mL of glyme under inert atmosphere at 65° C. 15.0 g (0.112 mol) of 2-(2-ethoxyethoxy)ethanol was slowly added to the flask and stirred at 65° C. for 1 h. The alkoxide was transferred to the dry 300 mL Parr reactor, stirred and heated at 65° C. for 1 h after which TFE gas was added. The pressure was maintained at ~50–60 PSI. A very slight exotherm (~5° C.) was initially observed. After 45 minutes, stirring was stopped and the reactor was cooled to room temperature. Excess TFE was carefully vented and the reactor contents transferred to a 500 mL Erlenmeyer flask. The mixture was diluted to 300 mL with pentane to effect complete precipitation of sodium salts. The mixture was filtered through a course frit funnel to remove sodium salts. The liquid fraction was rotary evaporated to give a clear yellow crude product. The crude product was vacuum fractionally distilled over potassium carbonate. 16.0 g (67% yield) of the desired product, 1-[2-(2-ethoxyethoxy)ethoxy]-1,2,2-trifluoroethene, was isolated at a boiling point of 39–41° C. (pressure ~1 mmHg, >99% purity by GC). $^{19}F$ NMR: $\delta=-123.4$ (dd, 1F J=56, 104 Hz, CF), $-130.2$ (dd, 1F J=104, 108, CF), $-135.1$ (dd, 1F J=56, 108 Hz, CF); $^{1}H$ NMR: $\delta=4.15$ (m, 2H, CFOCF$_2$), 3.75 (t, 2H, OCH$_2$), 3.7–3.45 (m, 6H, OCH$_2$), 1.2(t, 3H, CH$_3$).

EXAMPLE 3

Preparation of 1-[2-(2-tert-butoxyethoxy)ethoxy]-1,2,2-trifluoroethene (Bu-TFVE)

Bu-TFVE was prepared by mixing 2.66 g of NaH (0.111 mol) and 1 g of 18-crown-6 with 135 mL of glyme under inert atmosphere at 65° C. 15.0 g (0.092 mol) of 2-(2-t-butoxyethoxy)ethanol was slowly added to the flask and stirred at 65° C. 1 h. The alkoxide was transferred to the dry 300 mL Parr reactor, stirred and heated at 65° C. for 1 h after which TFE gas was added. The pressure was maintained at ~50–60 PSI. A very slight exotherm (~5° C.) was initially observed. After 45 minutes, stirring was stopped and the reactor was cooled to room temperature. Excess TFE was carefully vented and the reactor contents transferred to a 500 mL Erlenmeyer flask. The mixture was diluted to 300 mL with pentane to effect complete precipitation of sodium salts. The mixture was filtered through a course frit funnel to remove sodium salts. The liquid fraction was rotary evaporated to give a clear yellow crude product. The crude product was vacuum fractionally distilled over potassium carbonate. 14.1 g (63% yield) of the desired product, 1-[2-(2-ethoxyethoxy)ethoxy]-1,2,2-trifluoroethene, was isolated at a boiling point of 26–27° C. (pressure 0.15 mmHg, >99% purity by GC). $^{19}F$ NMR: $\delta=-123.5$ (dd, 1F J=56, 104 Hz, CF), $-130.3$ (dd, 1F J=104, 108, CF), $-135.1$ (dd, 1F J=56, 108 Hz, CF); $^{1}H$ NMR: $\delta=4.15$ (m, 2H, CFOCF$_2$), 3.75 (t, 2H, OCH$_2$), 3.65–3.45 (m, 4H, OCH$_2$), 1.2(s, 9H, C(CH$_3$)$_3$).

Synthesis of New Fluoropolymers from New Fluoromonomers

Fluoropolymers have been synthesized from the new fluoromonomers yielding homo-, co- and ter-polymers having the generic structure of —[CF$_2$CF{(OCH$_2$CH$_2$)$_n$OR}]$_m$—. The polymers have been synthesized by redox-initiated-emulsion (see Examples 4–6) and free radical bulk polymerization (see Example 7). Four homopolymers have been prepared to date: (1) n=2, R=ethyl; (2) n=2, R=t-butyl; (3) n=2, R=H; (4) n=1, R=phenyl. Examples of copolymers prepared in accordance with the present invention comprising the novel fluoromonomers are characterized by different monomer ratios of: (1) n=2, R=ethyl and n=2 and R=t-butyl; and (2) n=2 and R=t-butyl and n=2 and R=H. (3) n=1 and R=phenyl, and ethyl vinyl ether (EVE) and (4) n=1 and R=phenyl and ethyl vinyl acetate (VA); (5) n=2, R=ethyl and EVE; and (6) n=2, R=ethyl and VA. An example of a terpolymer that has been prepared with different monomer ratios is characterized by: n=2, R=ethyl and n=2, R=t-butyl and n=2,R=H.

Figure 3:
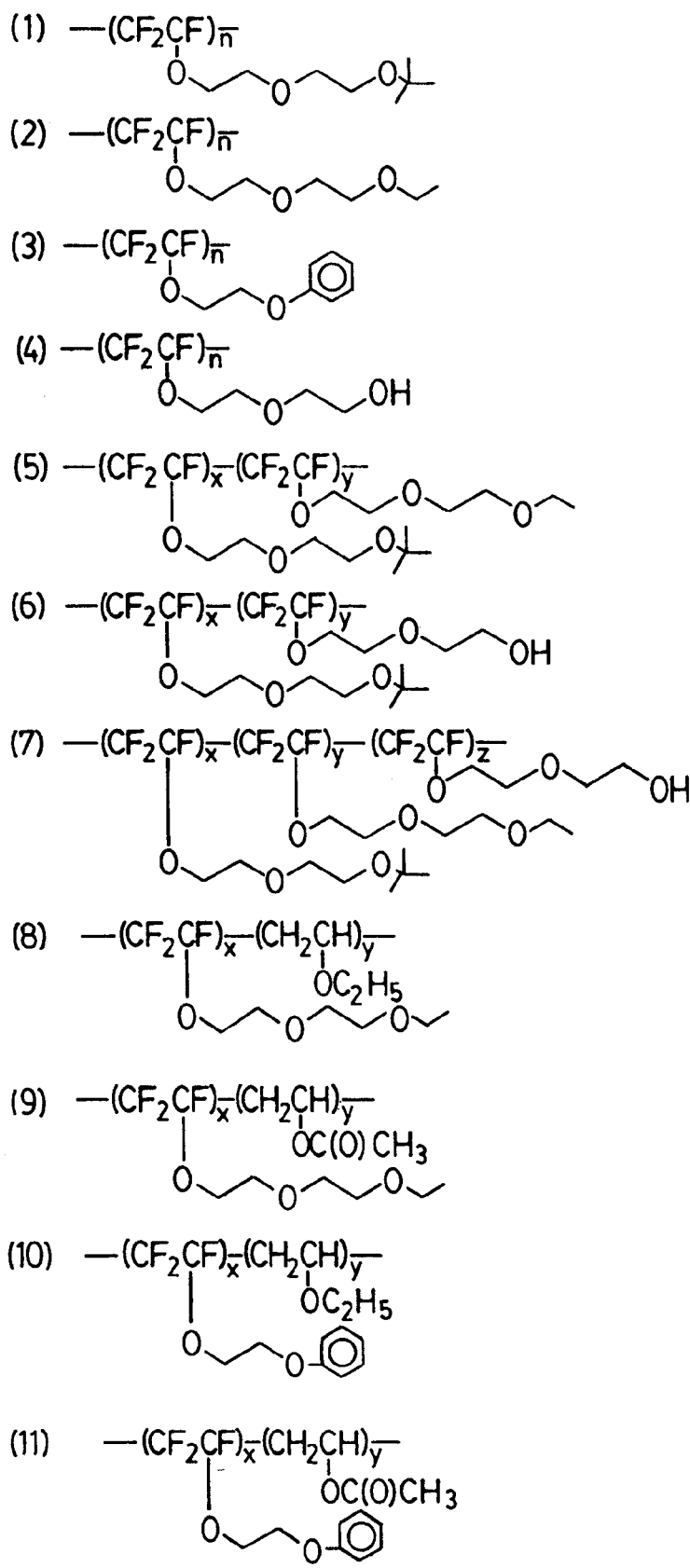
FIG. 3 gives the chemical formula for the polymers and copolymers synthesized in accordance with the present invention, 1) poly(diethylene glycol mono-tertiary-butyl ether monotrifluoroethylene ether),
2) poly(diethylene glycol monoethyl ether monotrifluoroethylene ether),
3) poly(ethylene glycol monophenyl ether monotrifluoroethylene ether),
4) poly(diethylene glycol mono-hydroxy ether monotrifluoroethylene ether),
5) poly(diethylene glycol mono-tertiary-butyl ether monotrifluoroethylene ether -co-diethylene glycol monoethyl ether monotrifluoroethylene ether),
6) poly(diethylene glycol mono-tertiary-butyl ether monotrifluoroethylene ether -co-diethylene glycol mono-hydroxy ether monotrifluoroethylene ether),
7) poly(diethylene glycol mono-tertiary-butyl ether monotrifluoroethylene ether -co-diethylene glycol monoethyl ether monotrifluoroethylene ether-co-diethylene glycol mono-hydroxy ether monotrifluoroethylene ether),
8) poly(diethylene glycol monoethyl ether monotrifluoroethylene ether-co-ethyl vinylether),
9) poly(diethylene glycol monoethyl ether monotrifluoroethylene ether-co-vinyl acetate),
10) poly(ethylene glycol monophenyl ether monotrifluoroethylene ether-co-ethyl vinyl ether),
11) poly(ethylene glycol monophenyl ether monotrifluoroethylene ether-co-vinyl acetate)

The following lists examples of homopolymers, copolymers and terpolymers that have been prepared (see FIG. 3 for chemical structures):

1) poly(diethylene glycol mono-tertiary-butyl ether monotrifluoroethylene ether);
2) poly(diethylene glycol monoethyl ether monotrifluoroethylene ether);
3) poly(ethylene glycol monophenyl ether monotrifluoroethylene ether);
4) poly(diethylene glycol mono-hydroxy ether monotrifluoroethylene ether);
5) poly(diethylene glycol mono-tertiary-butyl ether monotrifluoroethylene ether co-diethylene glycol monoethyl ether monotrifluoroethylene ether);
6) poly(diethylene glycol mono-tertiary-butyl ether monotrifluoroethylene ether -co-diethylene glycol mono-hydroxy ether monotrifluoroethylene ether);
7) poly(diethylene glycol mono-tertiary-butyl ether monotrifluoroethylene ether -co-diethylene glycol monoethyl ether monotrifluoroethylene ether-co-diethylene glycol mono-hydroxy ether monotrifluoroethylene ether);
8) poly(diethylene glycol monoethyl ether monotrifluoroethylene ether-co-ethyl vinyl ether)
9) poly(diethylene glycol monoethyl ether monotrifluoroethylene ether-co-vinyl acetate)
10) poly(ethylene glycol monophenyl ether monotrifluoroethylene ether-co-ethyl vinyl ether)
11) poly(ethylene glycol monophenyl ether monotrifluoroethylene ether-co-vinyl acetate).

Redox Emulsion Polymerization of Novek 1-(2alkoxy-ethoxy)-1,2,2-trifluoroethenes The three TFVE monomers, Et-TFVE, t-Bu-TFVE and Ph-TFVE, were prepared as described herein. Polymers were characterized for molar mass using a Waters gel permeation chromatograph, THF mobile phase and polystyrene standards. $^{1}H$ and $^{19}F$ NMR spectra were obtained at 300 and 282.2 MHz respectively on a Varian Gemini spectrometer using TMS and CFCl$_3$ as external references and deuterated chloroform as the solvent. Glass transition temperatures ($T_g$) were measured under an inert nitrogen atmosphere at a heating rate of 10° C./min.

EXAMPLE 4

Redox Emulsion Polymerization of Et-TFVE

To a 100 ml round bottom flask 30 mL of deionized water containing $5.2\times10^{-5}$ g Fe(ll) as FeSO$_4$.7H$_2$O was added. The flask was cooled and maintained at 20° C. using a temperature controlled water bath and residual oxygen was removed using a nitrogen purge for 1 h. To the flask was added 0.15 g Na$_2$HPO$_4$, 0.30 g sodium dodecyl sulfate, and 50 mg NaHSO$_3$. 3.0 g of Et-TFVE followed by 50 mg of (NH$_4$)$_2$S$_2$O$_8$ were added to the flask. The flask was stirred for 2 d at 20° C. at which time, ~0.5 ml of conc. HCl was added to the flask to precipitate the polymer. The polymer was collected by centrifugation, dissolved in ethanol and precipitated into water (twice). The polymer was dried at 40° C. in a vacuum oven, resulting in 2.1 g of a transparent, highly viscous polymer. GPC: Mn=8,520 g/mol, Mw=23,000 g/mol. $^1$H NMR: δ=5.7 (broad d, CF$_2$CFH), δ=4.15 (broad s, 2H, CFOCH$_2$), 3.8–3.4 (broad m, 8H, OCH$_2$), 1.2 (t, 3H, CH$_3$). $^{19}$F NMR: δ=−111 to −117 (broad m, 2F, CF$_2$), −134 to −137 (broad m, 1F, CF).

Figure 4:
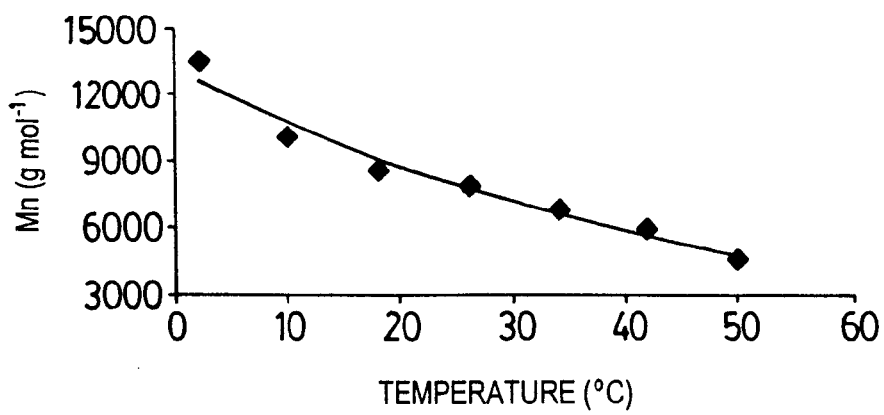
FIG. 4 is a plot of molecular weight versus synthesis temperature showing that a range of poly(Et-TFVE)s could be prepared by controlling the temperature of the polymerization, higher molecular weight polymers were prepared at lower temperatures.

A series of Et-TFVE polymers were prepared between 2 and 50° C. (using K$_2$S$_2$O$_8$ instead of (NH$_4$)$_2$S$_2$O$_8$) at constant initiator concentrations (~6×10$^{-3}$ M, 1 mol % relative to monomer). As shown in FIG. 4, M$_n$ increased with decreasing temperature and reached a maximum of approximately 13,000 gmol$^{-1}$ (M$_w$=33,800 gmol$^{-1}$) at the lowest practical temperature of 2° C. The PDIs for all polymers were typically between 2.6 and 3.6, with those polymers synthesized at the lower temperatures having the lower PDIs. The polymer yields were typically between 60 and 70% after 2 to 4 d. All poly(Et-TFVE)s were transparent, highly viscous liquids, with glass transition temperatures (T$_g$) of −62° C. to −60° C. for poly(Et-TFVE) samples with M$_n$'s of 4,000 gmol$^{-1}$ to 13,000 gmol$^{-1}$, respectively. Poly(Et-TFVE) decomposed in one stage, with an onset temperature at 300° C., 10% mass loss at 327° C. and 85% mass loss at 400° C.

EXAMPLE 5

Redox Emulsion Polymerization of Bu-TFVE

To a 100 ml round bottom flask 30 mL of deionized water containing 5.2×10$^{-5}$ Fe(II) as FeSO$_4$.7H$_2$O was added. The flask was cooled and maintained at 20° C. using a temperature controlled water bath and residual oxygen was removed using a nitrogen purge for 1 h. To the flask was added 0.15 g Na$_2$HPO$_4$, 0.30 g sodium dodecyl sulfate, and 50 mg NaHSO$_3$. 3.0 g of Bu-TFVE followed by 50 mg of (NH$_4$)$_2$S$_2$O$_8$ were added to the flask. The flask was stirred for 2 d at 20° C. at which time, ~0.5 ml of conc. HCl was added to the flask to precipitate the polymer. The polymer was collected by centrifugation, dissolved in ethanol and precipitated into water (twice). The polymer was dried at 40° C. in a vacuum oven, resulting in 2.4 g a transparent, highly viscous polymer. GPC: Mn=9100 g/mol, Mw=27,300 g/mol. $^1$H NMR: δ=5.7 (broad d, CF$_2$CFH), δ=4.15 (broad s, 2H, CFOCH$_2$), 3.8–3.4 (broad m, 6H, OCH$_2$), 1.2 (s, 9H, C(CH$_3$)$_3$). $^{19}$F NMR: δ=−111 to −117 (broad m, 2F, CF$_2$), −134 to −137 (broad m, 1F, CF). Poly(Bu-TFVE) was a transparent, highly viscous liquid, with a glass transition temperature (T$_g$) of −60° C. Poly(Bu-TFVE) decomposed in two stages, with an onset temperature in the first stage at 115° C. and 10% mass loss at 140° C. Approximately 30% mass loss was observed in the first stage of decomposition. In the second stage of decomposition, the onset temperature was observed at 280° C., an additional 10% (i.e., 40% total) mass loss at 330° C., and 90% mass loss at 400° C.

EXAMPLE 6

Redox Emulsion Polymerization of Ph-TFVE

To a 100 ml round bottom flask 30 mL of deionized water containing 5.2×10$^{-5}$ g Fe(II) as FeSO$_4$.7H$_2$O was added. The flask was cooled and maintained at 20° C. using a temperature controlled water bath and residual oxygen was removed using a nitrogen purge for 1 h. To the flask was added 0.15 g Na$_2$HPO$_4$, 0.30 g sodium dodecyl sulfate, and 200 mg NaHSO$_3$. 3.0 g of Ph-TFVE followed by 200 mg of (NH$_4$)$_2$S$_2$O$_8$ were added to the flask. The flask was stirred for 2 d at 20° C. at which time the contents were poured into 150 mL of methanol to precipitate the polymer. The polymer was washed several times with water and finally with methanol. The polymer was dried at 40° C. under vacuum, resulting in 2 g of a white solid polymer. GPC: Mn=23,000 g/mol, Mw=57,500 g/mol. $^1$H NMR: δ=7.4–6.6 (broad m, 5H, Ph), 4.2 (broad s, 2H, CFOCH$_2$), 3.8 (broad s, 2H, OCH$_2$).; $^{19}$F NMR: δ=−111 to −115 (broad d, J=~85 Hz, 2F, CF$_2$), −134 to −136 (broad m, 1F, CF). Poly(Ph-TFVE) was a white powder and had a T$_g$ of 23° C.

EXAMPLE 7

Bulk Homopolymerization of Ph-TFVE

The initiator, 2,2'-azobisisobutyronitrile (AIBN, 15 mg, 2 mol %), was added to a 2 ml glass vial that was sealed with a screw cap and a septum and purged with nitrogen (5 min.). To the vial was added 1.00 g of Ph-TFVE. The vial was placed in a 55° C. oven for 3 d, after which most of the unreacted monomer was removed under vacuum (P 0.1 mmHg, T=55° C). The $^1$H NMR and $^{19}$F NMR data are in accord with those reported for the emulsion polymerized Ph-TFVE. As determined by GPC, bulk poly(Ph-TFVE) had a M$_n$ of 8,100 gmol$^{-1}$ and a M$_w$ of 15,400 gmol$^{-1}$.

Copolymer Synthesis

EXAMPLE 8

Synthesis of Poly(Et-TFVE-co-Bu-TFVE) by Redox-initiated Emulsion

To a 100 mL round bottom flask equipped with a magnetic stirrer and nitrogen purge, 5.2×10$^{-5}$ g of Fe(II) (as FeSO$_4$.7H$_2$O) was dissolved in 30 ml of deionized water. Dissolved oxygen was removed using a nitrogen purge (45 min.). Sodium hydrogen phosphate (0.15 g), sodium dodecylsulfate (0.20 g), and sodium hydrogensulfite (50 mg) were added to the flask. The temperature of the flask was adjusted to the desired polymerization temperature (20° C.). Potassium persulfate (50 mg) was added to the flask prior to the addition of monomers (4.35–4.55 g). The monomers were polymerized for 2 days after which ~0.5 ml of concentrated HCl was added followed by centrifugation. The polymer was dissolved in ethanol and then precipitated in water (twice) before drying under vacuum (P 0.1 mmHg, room temperature, RT). The yield was maintained between 15 and 30% to minimize copolymer compositional drift. $^1$H NMR: δ=5.7 (broad d, CF$_2$CFH), 4.15 (broad s, 4H, CFOCH$_2$), 3.8–3.4 (broad m, 14H, OCH$_2$), 1.2 (m, 12H, C(CH$_3$)$_3$ and CH$_3$). A series of copolymers were prepared by varying the composition of Et-TFVE and Bu-TFVE monomers in the feed. The $^1$H NMR data were used to calculate copolymer composition. As shown in Table 1, seven polymers were prepared with Bu-TFVE compositions ranging from 0 to 100 mol %. The yield for all polymers was limited to between 15% and 32% to minimize copolymer compositional drift. The T$_g$ of poly(Et-TFVE-co-Bu-TFVE), having 50 mol % Et-TFVE, was similar to that of the homopolymers, with a T$_g$ of 63° C. The 50/50 copolymer of poly(Et-TFVE-co-Bu-TFVE) exhibited thermal behaviour between the two homopolymers, having a two stage thermal decomposition. In the first stage of decomposition (at 140° C), the copolymer lost 15% of its mass relative to the 30% lost by the Bu-TFVE homopolymer.

EXAMPLE 9

Figure 5:
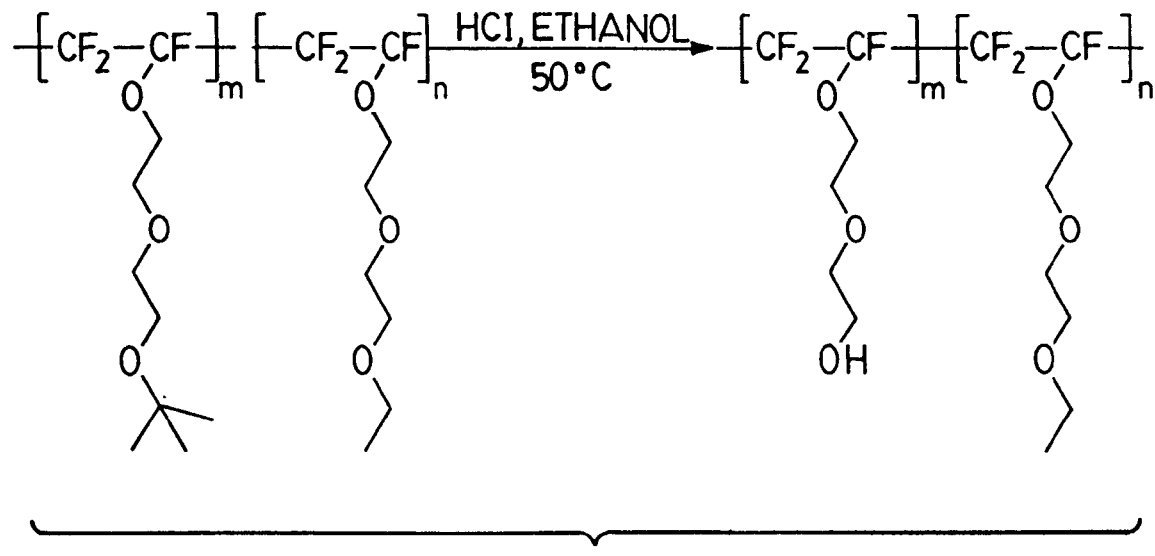
FIG. 5 shows the reaction to synthesize poly(Et-TFVE-co-TFVE-OH) by hydrolyzing the t-butoxy groups of poly(Et-TFVE-co-Bu-TFVE.

Synthesis of Poly(Et-TFVE-co-TFVE-OH) by Deprotection of the t-butyl Group of Bu-TFVE to TFVE-OH Copolymers of Et-TFVE and Bu-TFVE were prepared with a range of Bu-TFVE contents in order to prepare polymers with a range of hydroxyl contents. As shown in FIG. 5, the tertiary-butoxy group was removed under acidic conditions, yielding hydroxyl reactive handles (TFVE-OH). To a 25 ml round bottom flask equipped with a magnetic stir bar, was added ~5 ml of ethanol in which 0.2–0.3 g of poly(Bu-TFVE) or poly(Bu-TFVE-co-Et-TFVE) was dissolved. To this solution was added 1–2 ml of concentrated HCl. The solution was heated at 50° C. for 2–4 h, with longer times being used to hydrolyze samples with greater Bu-TFVE contents. The hydrolyzed polymers were recovered by drying under vacuum (P=0.1 mmHg, 50° C.) for at least 10 h. $^1$H NMR: δ=5.7 (broad d, $CF_2CFH$), 4.15 (broad s, 4H, $CFOCH_2$), 3.8–3.4 (broad m, 14H, $OCH_2$), 2.5 (s, 1H, OH), 1.2 (t, 3H, $CH_3$).

Table 2 summarizes the GPC data for a series of copolymer compositions. We confirmed that the polymers were hydrolyzed by both $^1$H NMR and FTIR. The $^1$H NMR data indicated a decrease in the integrated ratio of methyl to methylene groups and the appearance of a hydroxyl peak at 2.4–3.5 ppm after hydrolysis; some methyl peaks were expected from the terminal ethyl group of Et-TFVE. Using the $^1$H NMR data all polymers were fully hydrolyzed to ≧99%. The FTIR spectra of hydrolyzed polymers showed both a broadening of the hydroxyl stretch at 3480 cm$^{-1}$ and its shift to lower wavenumbers with increased TFVE-OH content. The $T_g$ of poly(Et-TFVE-co-TFVE-OH) was measured for different copolymer compositions, from 0% to 100% TFVE-OH, as determined from Bu-TFVE compositions and assuming 100% de-protection.

Figure 6:
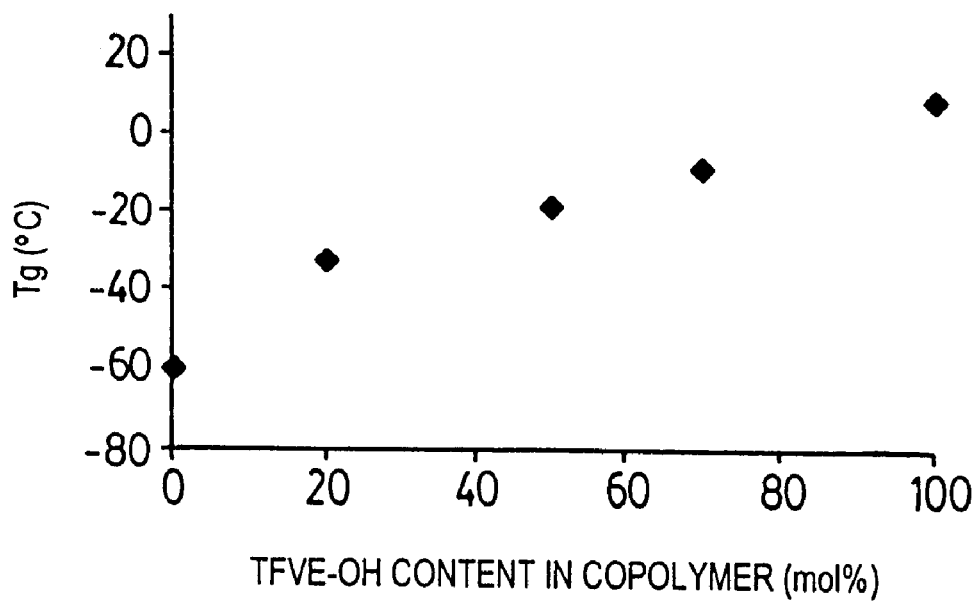
FIG. 6 is a plot of the glass transition temperature of poly(Et-TFVE-co-TFVE-OH) showing that it increases with increasing TFVE-OH content, reaching a maximum for the homopolymer, poly(TFVE-OH)

The glass transition temperature ($T_g$) increased with hydroxyl content, from −61° C. for poly(Bu-TFVE) to +9° C. for poly(TFVE-OH), as shown in FIG. 6. The physical nature of the polymers changed with hydroxyl content, from a viscous liquid for poly(Bu-TFVE) to a white tacky solid for poly(TFVE-OH). Poly(TFVE-OH) had an onset temperature of 150° C. and 10% mass loss at 205° C. At 400° C. poly(TFVE-OH) lost 60% of its mass whereas other polymers lost over 85% of their mass. Poly(TFVE-OH) lost 85% of its mass at temperatures exceeding 650° C. The copolymer, poly(Et-TFVE-co-TFVE-OH), demonstrated a thermal behaviour between the two homopolymers, yet had a profile more similar to that of poly(Et-TFVE) than poly (TFVE-OH).

Copolymer Synthesis by Redox Emulsion Polymerization of Novel Trifluorovinyl Ethers and Hydrocarbon Monomers

EXAMPLE 10

Copolymerization of Ph-TFVE with Ethyl Vinyl Ether (EVE)

In each of examples 10a) and 10b) below 30 mL of deionized water containing 5.2×10$^{-5}$ g Fe(II) as $FeSO_4.7H_2O$ was added to a 100 ml round bottom flask. The flask was cooled and maintained at 20° C. using a temperature controlled water bath and residual oxygen was removed using a nitrogen purge for 1 h. To the flask was added 0.15 g $Na_2HPO_4$, 0.30 g sodium dodecyl sulfate, and 50 mg $NaHSO_3$.

10a) A mixture of 3.0 g of Ph-TFVE (13.7 mmol) and 1.0 g of EVE (13.9 mmol) was added to the flask followed by 50 mg of $K_2S_2O_8$. The flask was sealed with a glass stopper and stirred at 20° C. for 48 h. The mixture was poured into 400 mL beaker containing 150 mL of methanol which resulted in the precipitation of a white polymer powder: poly(Ph-TFVE-co-EVE). The polymer was filtered and washed several times with water and finally with methanol. The polymer was dried to constant weight in a vacuum oven (40° C.). Yield 1.76 g. GPC (polystyrene standards); Mn: 97,500 g/mol, Mw: 205,000 g/mol, PDI: 2.10. Composition by $^1$H NMR: 54 mol % Ph-TFVE.

10b) A mixture of 3.0 g of Ph-TFVE (13.7 mmol) and 1.0 g of EVE (13.9 mmol) was added to the flask followed by 50 mg of $(NH_4)_2S_2O_8$. The flask was sealed with a glass stopper and stirred at 20° C. for 48 h. The mixture was poured into 400 mL beaker containing 150 mL of methanol which resulted in the precipitation of a white polymer powder: poly(Ph-TFVE-co-EVE). The polymer was filtered and washed several times with water and finally with methanol. The polymer was dried to constant weight in a vacuum oven (40° C.). Yield 3.04 g. GPC (polystyrene standards); Mn: 65,500 g/mol, Mw: 198,000 g/mol, PDI: 3.02. Composition by $^1$H NMR: 51 mol % Ph-TFVE.

EXAMPLE 11

Copolymerization of Et-TFVE with EVE

In each of examples 11a), 11b) and 11c) below 30 mL of deionized water containing 5.2×10$^{-5}$ g Fe(II) as $FeSO_4.7H_2O$ was added to a 100 ml round bottom flask was added. The flask was cooled and maintained at 20° C. using a temperature controlled water bath and residual oxygen was removed using a nitrogen purge for 1 h. To the flask was added 0.15 g $Na_2HPO_4$, 0.30 g sodium dodecyl sulfate, and 50 mg $NaHSO_3$.

11a) A mixture of 3.0 g of Et-TFVE (14.0 mmol) and 1.0 g of EVE (13.9 mmol) was added to the flask followed by 50 mg of $(NH_4)_2S_2O_8$. The flask was sealed with a glass stopper and stirred at 20° C. for 48 h. The polymer was precipitated by addition of approximately 0.5 mL of concentrated HCl. The polymer was collected, dissolved in ethanol, and precipitated (twice) from water. The polymer was dried to constant weight in a vacuum oven (40° C.) which resulted in a clear, highly viscous material: poly(Et-TFVE-co-EVE). Yield 2.48 g. GPC (polystyrene standards); Mn: 25,400 g/mol, Mw: 92,700 g/mol, PDI: 3.65. From $^1$H NMR: 70 mol % Et-TFVE incorporated in copolymer.

11b) A mixture of 2.8 g of Et-TFVE (13.1 mmol) and 1.2 g of EVE (16.6 mmol) was added to the flask followed by 50 mg of $(NH_4)_2S_2O_8$. The flask was sealed with a glass stopper and stirred at 20° C. for 15 h. The polymer was precipitated by addition of approximately 0.5 mL of concentrated HCl. The polymer was collected, dissolved in ethanol, and precipitated (twice) from water. The polymer was dried to constant weight in a vacuum oven (40° C.) which resulted in a clear, highly viscous material: poly(Et-TFVE-co-EVE). Yield 2.1 g. GPC (polystyrene standards); Mn: 35,000 g/mol, Mw: 119,700 g/mol, PDI: 3.42. Composition by $^1$H NMR: 55 mol % Et-TFVE incorporated into the copolymer.

11c) A mixture of 2.8 g of Et-TFVE (13.1 mmol) and 1.0 g of EVE (16.6 mmol) was added to the flask followed by 50 mg of $(NH_4)_2S_2O_8$. The flask was sealed with a glass stopper and stirred at 20° C. for 48 h. The polymer was precipitated by addition of approximately 0.5 mL of concentrated HCl. The polymer was collected, dissolved in ethanol, and precipitated (twice) from water. The polymer was dried to constant weight in a vacuum oven (40° C.) which resulted in a clear, highly viscous material: poly(Et-TFVE-co-EVE). Yield 3.2 g. GPC (polystyrene equivalents); Mn: 36,800 g/mol, Mw: 180,100 g/mol, PDI: 4.89. From $^1$H NMR; 50 mol % Et-TFVE incorporated in the copolymer.

EXAMPLE 12

Copolymerization of Ph-TFVE with Vinyl Acetate (VA)

In each of Examples 12a, 12b and 12c below 30 mL of deionized water containing $5.2 \times 10^{-5}$ Fe(II) as $FeSO_4 \cdot 7H_2O$ was added to a 100 ml round bottom flask. The flask was cooled and maintained at 20° C. using a temperature controlled water bath and residual oxygen was removed using a nitrogen purge for 1 h.

12a) To the flask was added 0.15 g $Na_2HPO_4$, 0.30 g sodium dodecyl sulfate, and 50 mg $NaHSO_3$. A mixture of 2.87 g of Ph-TFVE (13.2 mmol) and 1.13 g of VA (13.1 mmol) was added to the flask followed by 50 mg of $(NH_4)_2S_2O_8$. The flask was sealed with a glass stopper and stirred at 20° C. for 48 h. The polymer was precipitated by addition to approximately 150 mL of methanol containing approximately 0.5 mL of concentrated HCl. The polymer was filtered and washed several times with water and finally with methanol. The polymer was dried to constant weight in a vacuum oven (40° C.) which resulted in a white, solid material: poly(Ph-TFVE-co-VA). Yield 0.8 g. GPC (polystyrene standards); Mn: 117,000 g/mol, Mw: 301,000 g/mol, PDI: 2.57. Composition by $^1H$ NMR: 39 mol % Ph-TFVE. $T_g$: 46° C.

12b) To the flask was added 0.15 g $Na_2HPO_4$, 0.30 g sodium dodecyl sulfate, and 100 mg $NaHSO_3$. A mixture of 2.70 g of Ph-TFVE (12.4 mmol) and 1.30 g of VA (15.1 mmol) was added to the flask followed by 100 mg of $(NH_4)_2S_2O_8$. The flask was sealed with a glass stopper and stirred at 20° C. for 24 h. The polymer was precipitated by addition to approximately 150 mL of methanol containing approximately 0.5 mL of concentrated HCl. The polymer was filtered and washed several times with water and finally with methanol. The polymer was dried to constant weight in a vacuum oven (40° C.) which resulted in a white, solid material: poly(Ph-TFVE-co-VA). Yield 1.3 g. GPC (polystyrene standards); Mn: 121,600 g/mol, Mw: 348,600 g/mol, PDI: 2.87. Composition by $^1H$ NMR: 40 mol % Ph-TFVE incorporated into the copolymer.

12c) To the flask was added 0.15 g $Na_2HPO_4$, 0.30 g sodium dodecyl sulfate, and 200 mg $NaHSO_3$. A mixture of 2.70 g of Ph-TFVE (12.4 mmol) and 1.30 g of VA (15.1 mmol) was added to the flask followed by 200 mg of $(NH_4)_2S_2O_8$. The flask was sealed with a glass stopper and stirred at 20° C. for 24 h. The polymer was precipitated by addition to approximately 150 mL of methanol containing approximately 0.5 mL of concentrated HCl. The polymer was filtered and washed several times with water and finally with methanol. The polymer was dried to constant weight in a vacuum oven (40° C.) which resulted in a white, solid material: poly(Ph-TFVE-co-VA). Yield 2.0 g. GPC (polystyrene standards); Mn: 141,000 g/mol, Mw: 378,000 g/mol, PDI: 2.68. Composition by $^1H$ NMR: 43 mol % Ph-TFVE incorporated into the copolymer.

EXAMPLE 13

Copolymerization of Et-TFVE with Vinyl Acetate (VA)

In each of Examples 13a), 13b) and 13c) below 30 mL of deionized water containing $5.2 \times 10^{-5}$ g Fe(II) as $FeSO_4 \cdot 7H_2O$ was added to a 100 ml round bottom flask. The flask was cooled and maintained at 20° C. using a temperature controlled water bath and residual oxygen was removed using a nitrogen purge for 1 h. To the flask was added 0.15 g $Na_2HPO_4$, 0.30 g sodium dodecyl sulfate, and 50 mg $NaHSO_3$.

13a) A mixture of 3.0 g of Et-TFVE (14.0 mmol) and 1.2 g of VA (13.9 mmol) was added to the flask followed by 50 mg of $(NH_4)_2S_2O_8$. The flask was sealed with a glass stopper and stirred at 20° C. for 24 h. The polymer was precipitated by addition to approximately 30 mL of methanol containing approximately 0.5 mL of concentrated HCl. The polymer was collected, dissolved in ethanol, and precipitated (twice) from water. The polymer was dried to constant weight in a vacuum oven (40° C.) which resulted in a clear, tacky, solid material: poly(Et-TFVE-co-VA). Yield 3.3 g. GPC (polystyrene standards); Mn: 39,500 g/mol, Mw: 227,000 g/mol, PDI: 5.75. Composition by $^1H$ NMR: 42 mol % Et-TFVE incorporated into the copolymer.

13b) A mixture of 2.7 g of Et-TFVE (12.6 mmol) and 1.3 g of VA (15.1 mmol) was added to the flask followed by 50 mg of $(NH_4)_2S_2O_8$. The flask was sealed with a glass stopper and stirred at 20° C. for 24 h. The polymer was precipitated by addition to approximately 30 mL of methanol containing approximately 0.5 mL of concentrated HCl. The polymer was collected, dissolved in ethanol, and precipitated (twice) from water. The polymer was dried to constant weight in a vacuum oven (40° C.) which resulted in a clear, tacky, solid material: poly(Et-TFVE-co-VA). Yield 2.8 g. GPC (polystyrene standards); Mn: 43,500 g/mol, Mw: 168,100 g/mol, PDI: 3.87. Composition by $^1H$ NMR: 42 mol % Et-TFVE incorporated into the copolymer.

13c) A mixture of 2.5 g of Et-TFVE (11.7 mmol) and 1.5 g of VA (17.4 mmol) was added to the flask followed by 50 mg of $(NH_4)_2S_2O_8$. The flask was sealed with a glass stopper and stirred at 20° C. for 24 h. The polymer was precipitated by addition to approximately 30 mL of methanol containing approximately 0.5 mL of concentrated HCl. The polymer was collected, dissolved in ethanol, and precipitated (twice) from water. The polymer was dried to constant weight in a vacuum oven (40° C.) which resulted in a clear, tacky, solid material: poly(Et-TFVE-co-VA). Yield 3.0 g. GPC (polystyrene standards); Mn: 41,300 g/mol, Mw: 217,400 g/mol, PDI: 5.26. Composition by $^1H$ NMR: 38 mol % Et-TFVE incorporated into the copolymer.

EXAMPLE 14

Modification of Hydroxyl-functionalized TFVE Polymers

Hydroxyl-functionalized fluoropolymers were prepared to allow facile modification with, for example, crosslinking reagents for coatings applications. As a demonstration of its availability, the hydroxyl-functionality in poly(Et-TFVE-co-TFVE-OH) was modified with the HDI crosslinking reagent using dibutyltin dilaurate catalysis at 60° C.

In a 10 ml beaker, 60 mg of poly(Et-TFVE-co-TFVE-OH), with 30 mol % hydroxyl content, and 94 mg of 1,6-hexamethylene diisocyanate (HDI) were dissolved in 4 ml of chloroform after which a trace amount dibutyltin dilaurate catalyst was added. Approximately 3 to 4 drops of solution were placed on the PTFE window of a disposable IR card and heated at 60° C. for up to 30 minutes. The modification reaction was monitored by FTIR by the disappearance of the isocyanate and hydroxyl peaks at 2275 $cm^{-1}$ and 3453 $cm^{-1}$, respectively. The remaining solution was cast in a disposable aluminum pan and heated at 60° C. for 1 h. The extent of modification/crosslinking was determined by gravimetric analysis by comparing the dry mass of crosslinked films before and after immersion in 5 ml of ethanol for 24 h. Un-crosslinked polymer readily dissolved in ethanol.

For poly(Et-TFVE-co-TFVE-OH), having 30 mol % TFVE-OH content, the polymer had the characteristic hydroxyl stretch at 3453 cm$^{-1}$. Upon addition of the crosslinking agent for 5 min. at RT, the characteristic isocyanate peak ($v_{N=C=O}$) was observed at 2275 cm$^{-1}$ as were two small peaks attributed to the urethane bonds at 1724 cm$^{-1}$ for $v_{C=O}$ and 3345 cm$^{-1}$ for $v_{N-H}$. After 10 minutes at 60° C., both hydroxyl and isocyanate peaks had diminished while the two characteristic urethane peaks had strengthened. After an additional 20 minutes (30 minutes total) at 60° C., the isocyanate peak at 2275 cm$^{-1}$ was no longer visible and the urethane peaks were predominant. The FTIR data indicated that crosslinking was complete within 30 minutes at 60° C. Gravimetric analysis indicated that at least 85% of the TFVE-OH groups of the copolymer were crosslinked.

EXAMPLE 15

Polymer Blends of Novel poly(TFVE)s and Hydrocarbon Polymers

The following example applies to solvent cast blends but those skilled in the art will understand that it also applies to thermal/melt blends comprising the novel trifluorovinyl ether polymers disclosed herein and hydrocarbon polymers, polyesters, polyamides, etc. Solvent cast blends were prepared by co-dissolving in chloroform polystyrene (PSt) with one of (a) poly(Et-TFVE) or (b) poly(Et-TFVE-co-TFVE-OH) (50/50) to form 5% w/v solutions. Polymer films were obtained by casting these solutions onto aluminum or poly(tetrafluoroethylene) (PTFE) pans and allowing the solvent to evaporate slowly overnight. The fluoropolymer content in the films varied from 0.05 to 5 wt % (relative to PSt content); the total mass of each blend was 0.20 g. The resulting films were surface characterized by dynamic water contact angles and x-ray photoelectron spectroscopy (XPS, 90° takeoff angle data shown) at the air-polymer interface. All blended films were translucent to opaque, depending upon the fluoropolymer content whereas the pure PSt film was transparent.

Figure 7:
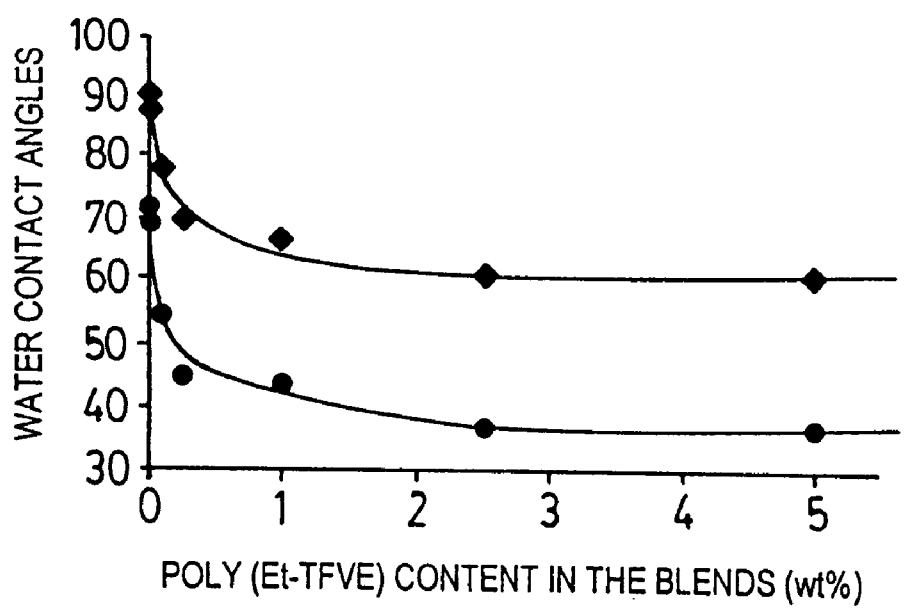
FIG. 7 is a plot of water contact angle versus polymer content of polymer blends illustrating the advancing (♦) and receding (○) water contact angles at the air-poly(Et-TFVE)/PSt blend interface decrease with increasing poly(Et-TFVE) content.
Figure 8:
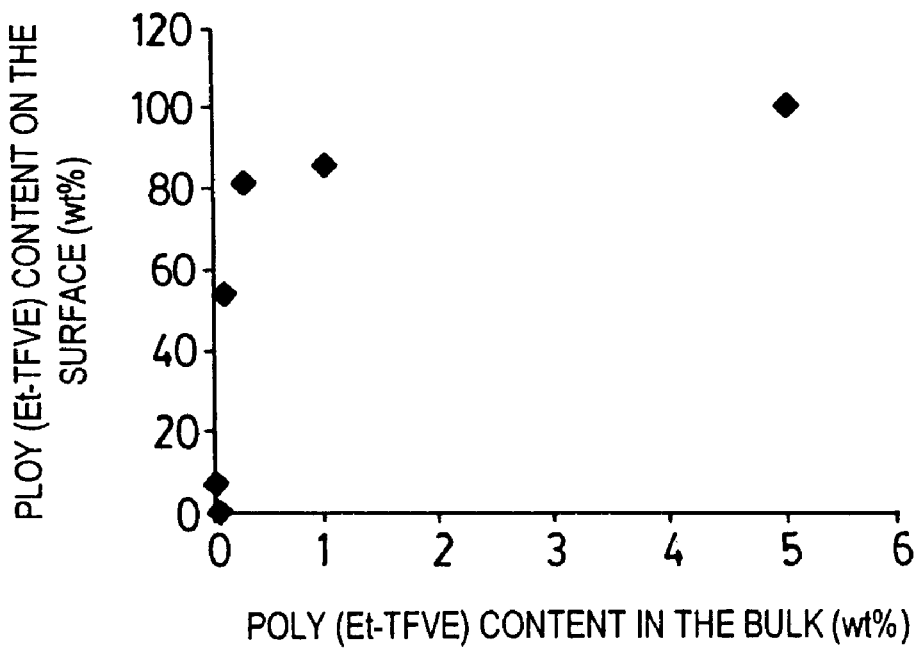
FIG. 8 is a plot showing the estimated surface poly(Et-TFVE) composition in poly(ET-TFVE)/PSt blends.
Figure 9:
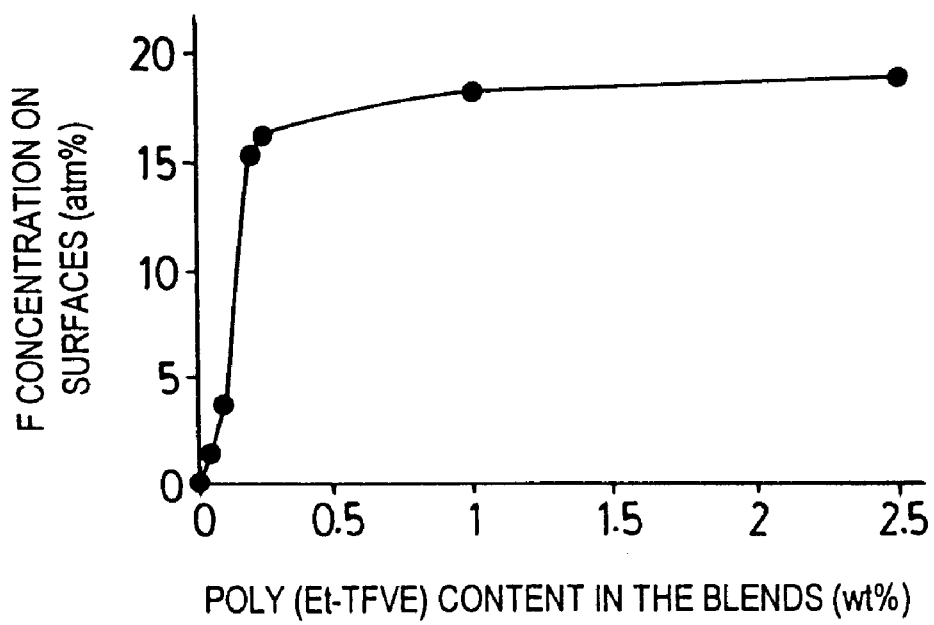
FIG. 9 is a plot of fluroine surface atomic concentration as determined by XPS (90° takeoff angle) increased at the air-polymer blend interface with increasing poly(Et-TFVE) content.

15a) PSt/Poly(Et-TFVE) Blends: FIG. 7 shows that the water contact angles decreased with increasing poly(Et-TFVE) content in the blend, indicating an increased hydrophilicity on the surface. The data indicates that the surface is saturated at 0.25 wt % of poly(Et-TFVE). The polymer composition on the surface can be estimated from Cassie's equation. As shown in FIG. 8, a poly(Et-TFVE) bulk composition of 0.25 wt % corresponds to a surface composition of 81 wt %, indicating that poly(Et-TFVE) is a surface active polymer. XPS measures surface atomic composition. FIG. 9 is the fluorine (F) atomic concentration on the surface related to the poly(Et-TFVE) content in the bulk. The F content increases with poly(Et-TFVE) content in the blend, saturating the surface between 0.25 wt % and 1 wt %. At 1 wt % the fluorine content is 19.6 mol % which indicates almost complete fluoropolymer coverage when compared to the theoretical F content of a fully fluorinated surface would have 21.4 mol % fluorine. The PTFE-blend interface was characterized by contact angle and XPS. At the PTFE-blend interface, the contact angle changed only slightly from 73° at 0 wt % poly(Et-TFVE) to 65° at 5 wt % poly(Et-TFVE). By XPS, the F content at the PTFE-blend interface was 12% at 0.10 wt %, 13% at 1.0 wt % and 17% at 5 wt %, indicating that at lower poly(Et-TFVE) content, the PTFE interface is enriched with poly(Et-TFVE) relative to the air-blend interface.

Figure 10:
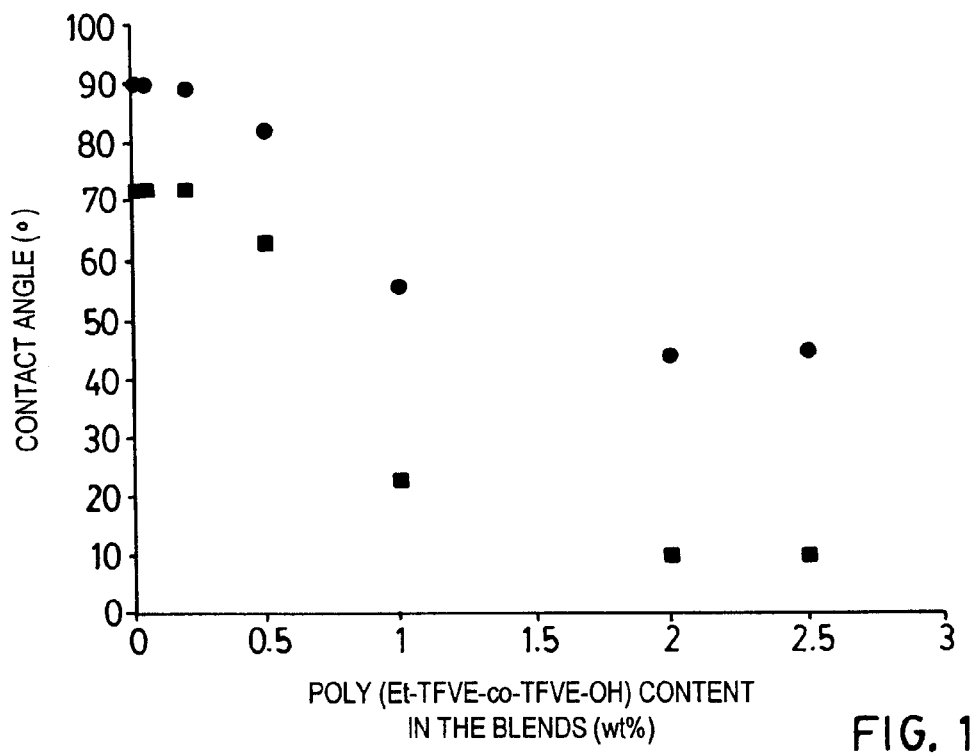
FIG. 10 shows plots of contact angle versus polymer contact in blends showing that the advancing (○) and receding (■) water contact angles at the air-poly(Et-TFVE-co-TFVE-OH)/PSt blend interface decrease with increasing poly(Et-TFVE-co-TFVE-OH) content.

15b) PSt/Poly(Et-TFVE-TFVE-OH) Blends: As shown in FIG. 10, the water contact angles decrease with increasing poly(Et-TFVE-co-TFVE-OH) content, reaching a surface saturation at 1.0 wt %.

EXAMPLE 16

Protein Adsorption to Films of PSt/Poly(TFVE) Blends

Thin films were prepared by solution casting from chloroform in aluminum pans at room temperature as described in Example 15. Five fluoropolymers, poly(Et-TFVE), poly(Et-TFVE-co-Bu-TFVE) (50/50), poly(Bu-TFVE) and two poly(Et-TFVE-co-TFVE-OH)s (50/50 and 30/70 mol/mol), were blended with PSt using a poly(TFVE) content of 0.25 wt % or 2.5 wt % relative to PSt content. Pure PSt films were used as controls.

Six samples of each blend (~51 mm$^2$) were cleaned with hexane, dried, washed with water, phosphate-buffered saline (PBS, pH 7.4, three times) and then immersed in PBS overnight. Protein adsorption was measured using I-125 radiolabeled fibrinogen and compared to non-radiolabeled fibrinogen which served as a control. Three of the six specimens were immersed into I-125 labeled fibrinogen and the other three into non-radiolabeled fibrinogen. The specimens were incubated at 37° C. for 2 h, washed three times with PBS, transferred to scintillation vials and the total protein adsorbed to each sample was calculated using a scintillation counter within a 5 minute time interval.

Figure 11:
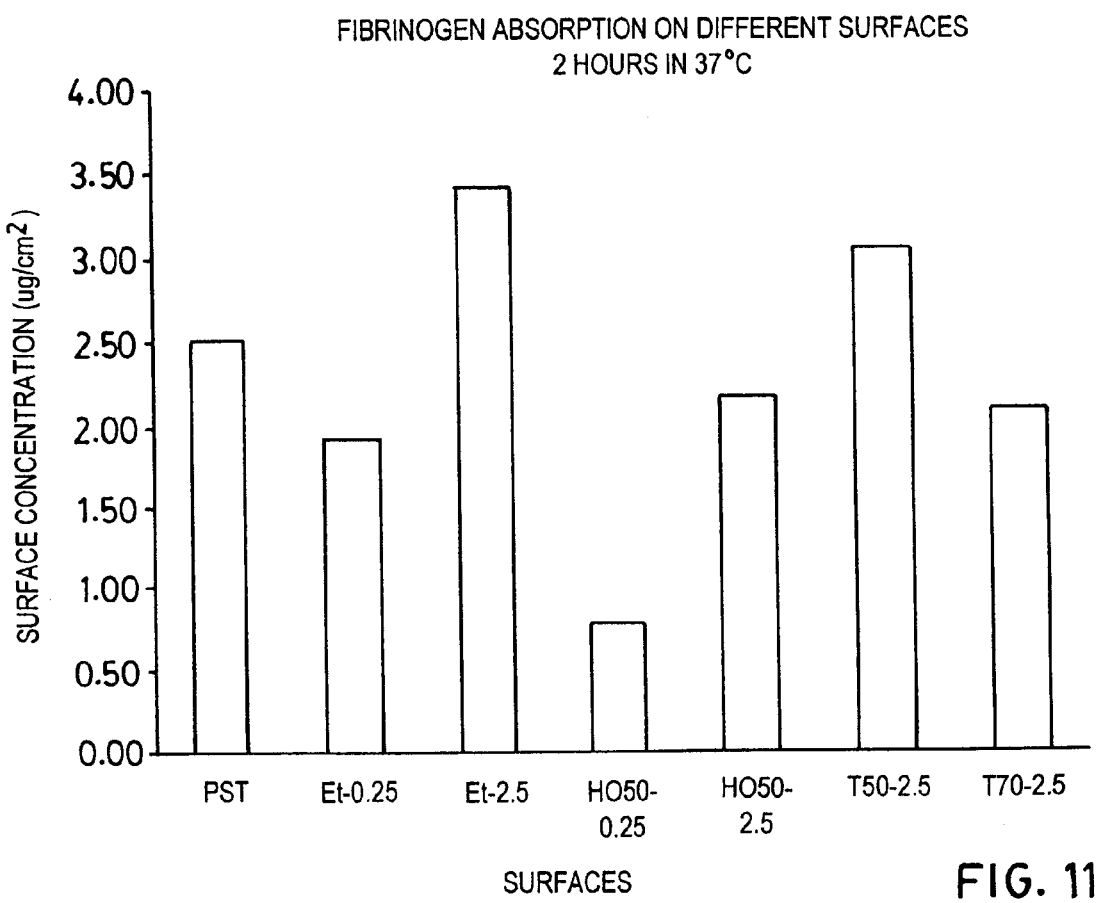
FIG. 11 shows protein (I-125 Fibrinogen) adsorption on different polymer blend surfaces, including from left to right,
1) PST: polystyrene,
2) Et-0.25: poly(ET-TFVE) content in blend is 0.25 wt %,
3) Et-2.5: poly(ET-TFVE) content in blend is 2.5 wt %,
4) 4HO50-0.25: poly(Et-TFVE-co-TFVE-OH) (50/50 mol/mol) content in blend is 0.25wt %,
5) HO50-2.5: poly(Et-TFVE-co-TFVE-OH) (50/50 mol/mol) content in blend is 2.5 wt %,
6) T50-2.5: poly(Et-TFVE-co-t-Bu-TFVE) (50/50 mollmol) content in blend is 2.5 wt %,
7) T70-2.5: poly(Et-TFVE-co-TFVE-OH) (30/70 mol/mol) content in blend is 2.5 wt %.

The results are summarized in FIG. 11. Compared with pure PSt background, poly(Et-TFVE) and poly(Et-TFVE-co-TFVE-OH) (50/50 mol/mol) at 0.25 wt % decreased fibrinogen adsorption. The lowest protein adsorption was observed for the blend with 0.25 wt % of poly(Et-TFVE-co-TFVE-OH) (50/50 mol/mol) in PSt; the total protein was reduced by ~60% relative to the PSt control. It will be understood that biologically useful materials exhibiting low protein absorption may be prepared using blends of some of these fluoropolymers blended with physiologically acceptable polymers. Therefore, blends of the fluoropolymers poly(Et-TFVE) and poly(Et-TFVE-co-TFVE-OH) (50/50 mollmol) with materials such as polystyrene, polypropylene, polyethylene, polysiloxanes and polyacrylates to mention just a few are useful in biological applications.

EXAMPLE 17

The present invention also encompasses other fluoromonomers of the following general formula CGJ=CL (OCH$_2$OCH$_2$)$_n$OR wherein n is an integer, R is a functional group, G and J are selected from the group consisting of chlorine, fluorine, trifluoromethyl and hydrogen, and wherein L is selected from the group consisting of chlorine, fluorine and hydrogen, and wherein at least one of G, J and L is fluorine. Non-limiting illustrative examples include

R represents an unsubstituted or inertly substituted hydrocarbyl group as previously defined.

While specific examples of homopolymers, copolymers and terpolymers synthesized in accordance with the present invention have been disclosed and exemplified above, it is to be understood by those skilled in the art that these examples are not meant to be interpreted as limiting in any way.

The copolymers may be prepared using the novel fluoromoners of the general formula $CF_2=CF(OCH_2CH_2)_nOR$, and a second fluoromonomer of the general formula $CF_2CXY$, wherein n is an integer and R represents an unsubstituted or inertly substituted hydrocarbyl group, and wherein X and Y may be hydrogen, halogen, unsubstituted hydrocarbyl groups, inertly substituted hydrocarbyl groups and any combination thereof.

In addition, the copolymers may be prepared using the novel fluoromonomers and fluoromonomers of the general formula CFXCYZ, wherein X, Y and Z may be hydrogen, halogen, unsubstituted hydrocarbyl and inertly substituted hydrocarbyl groups and any combination thereof.

Copolymers may be produced using the novel fluoromoners of the general formula $CF_2=CF(OCH_2CH_2)_nOR$ and monomers having the generic formula CXYCAB, wherein n is an integer and R is a functional group comprising unsubstituted hydrocarbyl or inertly substituted hydrocarbyl groups, and wherein X, Y, A, B may be hydrogen, halogen, unsubstituted hydrocarbyl groups, inertly substituted hydrocarbyl groups and any combination thereof.

Graft copolymers may be produced comprising a polymer graft and a polymer backbone. The backbone may comprise a polymer such as polystyrene, polyurethane, polyester, polyether, polyethylene, polypropylene, poly(carbonate), poly(anhydride), poly(vinyl chloride), poly(acrylonitrile), poly($\alpha$-hydroxyesters), poly(tetrafluoroethylene), poly(vinylidene fluoride), poly(chlorotrifluoroethylene), nylon, poly(ethylene terephthalate), poly(amide), poly(amine), poly(amino acid), poly(acrylate), poly(acetate) and any combination thereof. The polymer graft comprises a fluoropolymer of the following general formula $-[CF_2CF\{(OCH_2CH_2)_nOR\}]_m-$, wherein n is an integer, m is an integer and R represents an unsubstituted or inertly substituted hydrocarbyl group.

Similarly, numerous fluoropolymer blends may be produced using for example the fluoromoner $CF_2=CF(OCH_2CH_2)_nOR$ (wherein n is an integer greater than or equal to 1 and R represents an unsubstituted or inertly substituted hydrocarbyl group) and a polymer such as polystyrene, polyurethane, polyester, polyether, polyethylene, polypropylene, poly(carbonate), poly(anhydride), poly(vinyl chloride), poly(acrylonitrile), poly($\alpha$-hydroxyesters), poly(tetrafluoroethylene), poly(vinylidene fluoride), poly(chlorotrifluoroethylene), nylon, poly(ethylene terephthalate), poly(amide), poly(amine), poly(amino acid), poly(acrylate), poly(acetate) and any combination thereof.

Alternatively, a fluoropolymer blend may be produced using the fluoropolymer $-[CF_2CF\{(OCH_2CH_2)_nOR\}]_m-$ and the above-noted polymers.

The foregoing description of the embodiments of the invention has been presented to illustrate the principles of the invention and not to limit the invention to the particular embodiments illustrated and described. It is intended that the scope of the invention be defined by all of the embodiments encompassed within the following claims and their equivalents.

TABLE 1

The copolymer composition of poly(Et-TFVE-co-Bu-TFVE) was calculated from $^1$H NMR data; the molecular weight and polydispersity were calculated by GPC; and Tg was measured by DSC.

| Monomer Copolymer feed: | | | | | | |
|---|---|---|---|---|---|---|
| Bu-TFVE (mol %) | Composition Bu-TFVE (mol%) | Yield (%) | $M_w$ (g/mol) | $M_n$ (g/mol) | PDI | Tg (° C.) |
| 0 | 0 | 32 | 18,400 | 8.65 | 2.12 | −6.1 |
| 10 | 11 | 27 | 12,200 | 6,700 | 1.82 | |
| 20 | 20 | 29 | 14,100 | 7,340 | 1.92 | |
| 30 | 24 | 15 | 10,300 | 6,335 | 1.63 | |
| 50 | 46 | 18 | 19,900 | 9,100 | 2.18 | −63 |
| 70 | 68 | 23 | 21,100 | 9,400 | 2.24 | |
| 100 | 100 | 28 | 39,300 | 12,400 | 3.21 | −60 |

TABLE 2

The molecular weight and polydispersity of poly(Et-TFVE-co-Bu-TFVE)

| Copolymer Yield Composition | | GPC data | | |
|---|---|---|---|---|
| Et-TFVE mol % | mass % | $M_w$ g/mol | $M_n$ g/mol | PDI |
| 90 | 42 | 11,440 | 6,170 | 1.85 |
| 70 | 45 | 24,600 | 7,860 | 3.12 |
| 54 | 60 | 36,500 | 9,220 | 3.96 |

REFERENCES

[1] Dixon, S. U.S. Pat. No. 2,917,548, 1959
[2] Okuhara, K., Baba, H., and Kojima, R. *Bull. Chem. Soc. Jap.* 1962, 35, 532–535
[3] Wall, L. A., Pummer, W. J. U.S. Pat. No. 3,277,068 1966
[4] Babb, D. A., Clememnt, K. S., Ezzell, B. R. U.S. Pat. No. 5,162,468, 1992
[5] Clement, K. S., Babb, D. A., Richey, W. F. U.S. Pat. No. 5,198,513, 1993
[6] Fritz, C. G., Moore, E. P., Jr., Selman, S. U.S. Pat. No. 3,114,778, 1963
[7] Harris, J. F. Jr., McCane, D. I., U.S. Pat. No. 3,180,895, 1965
[8] Moore, E. P. Jr., Milian, A. S. Jr., Eleuterio, H. S. U.S. Pat. No. 3,250,808, 1966
[9] Farnham, W .B. U.S. Pat. No. 5,391,796, 1995
[10] Pellerite, M. J. *J. Fluorine Chem.* 1990, 49, 43–46
[11] Ezzell, B. R., Carl, W. P., Mod, W. A. U.S. Pat. No. 4,337,211, 1982
[12] Ezzell, B. R., Carl, W. P., Mod, W. A. U.S. Pat. No. 4,515,989, 1985
[13] Modern Fluoropolymers: High Performance Polymers for diverse Applications (Scheirs, J., Ed.) John Wiley & Sons, 1997
[14] Shoichet, M. S., McCarthy, T. J. Macromolecules 1991, 24, 982–986
[15] Feiring, A. E. in Organofluorine Chemistry: Principles and Commercial Applications (Banks, R. E., Tatlow, J. C., Smart, B. E., Eds.) Plenum Press: NY 1994, chap. 15
[16] Prime, K. L.; Whitesides, G. M. *J. Am. Chem. Soc.* 1993, 115, 10714–21
[17] Shoichet, M. S.; Winn, S. R.; Athavale, S.; Harris, J. M.; Gentile, F. T. *Biotechnol. & Bioeng.* 1994, 43, 563–572
[18] Tong, Y. W.; Shoichet, M. S. *J. Biomed. Mater. Res.* 1998, 42, 85–95

[19] Costello, C. A.; McCarthy, T. J. *Macromolecules* 1987, 20, 2819–28

Therefore what is claimed is:

1. A fluoropolymer of the following general formula (II), comprising:

$$-[CF_2CF\{(OCH_2CH_2)_nOR\}]_m- \qquad (II)$$

wherein n is an integer, m is an integer, and wherein R represents an unsubstituted or inertly substituted hydrocarbyl group, said fluoropolymer having a fluorocarbon backbone.

2. A copolymer, comprising:
a first fluoromonomer of the general formula $CF_2=CF(OCH_2CH_2)_nOR$, and a second fluoromonomer of the general formula $CF_2CXY$, wherein n is an integer, and wherein R represents an unsubstituted or inertly substituted hydrocarbyl group, and wherein X and Y are selected from the group consisting of hydrogen, halogen, hydrocarbyl groups, inertly substituted hydrocarbyl groups and any combination thereof.

3. The copolymer according to claim 2 wherein said copolymer is selected from the group consisting of random, block, alternating, branched and graft copolymers.

4. The copolymer according to claim 3 wherein said copolymer is one of a random and alternating copolymer prepared by a process of free radical bulk polymerization.

5. The copolymer according to claim 3 wherein said copolymer is one of a random and alternating copolymer prepared by a process of redox emulsion polymerization.

6. A copolymer, comprising:
a first fluoromonomer of the general formula $CF_2=CF(OCH_2CH_2)_nOR$, and a second fluoromonomer of the general formula CFXCYZ, wherein n is an integer, wherein R represents an unsubstituted or inertly substituted hydrocarbyl group, and wherein X, Y and Z are selected from the group consisting of hydrogen, halogens, unsubstituted hydrocarbyl and inertly substituted hydrocarbyl groups and any combination thereof.

7. The copolymer according to claim 6 wherein said copolymer is selected from the group consisting of random, block, alternating, branched and graft copolymers.

8. The copolymer according to claim 7 wherein said copolymer is one of a random and alternating copolymer prepared by a process of free radical bulk polymerization.

9. The copolymer according to claim 7 wherein said copolymer is one of a random and alternating copolymer prepared by a process of redox emulsion polymerization.

10. A copolymer, comprising:
a first fluoromonomer having a general formula $CF_2=CF(OCH_2CH_2)_nOR$ and a second monomer having a generic formula CXYCAB, wherein n is an integer and wherein R represents an unsubstituted or inertly substituted hydrocarbyl group, and wherein X, Y, A, B are selected from the group consisting of hydrogen, halogen, unsubstituted hydrocarbyl groups, inertly substituted hydrocarbyl groups and any combination thereof.

11. The copolymer according to claim 10 wherein said copolymer is selected from the group consisting of random, block, alternating, branched and graft copolymers.

12. The copolymer according to claim 11 wherein said copolymer is one of a random and alternating copolymer prepared by a process of free radical bulk polymerization.

13. The copolymer according to claim 11 wherein said copolymer is one of a random and alternating copolymer prepared by a process of redox emulsion polymerization.

14. A halopolymer of the following general formula, comprising:

$$-[CGJCL\{(OCH_2CH_2)_nOR\}]_m-$$

wherein n is an integer, m is an integer and R represents an unsubstituted or inertly substituted hydrocarbyl group, and wherein G and J are selected from the group consisting of chlorine, fluorine, trifluoromethyl and hydrogen, and wherein L is selected from the group consisting of chlorine, fluorine and hydrogen, and wherein at least one of G, J and L is fluorine, said halopolymer having a halocarbon backbone.

15. A copolymer, comprising:
a fluoromonomer of the general formula $CGJ=CL(OCH_2CH_2)_nOR$, wherein n is an integer and R represents an unsubstituted or inertly substituted hydrocarbyl group, G and J are selected from the group consisting of chlorine, fluorine, trifluoromethyl and hydrogen, and wherein L is selected from the group consisting of chlorine, fluorine and hydrogen, and wherein at least one of G, J and L is fluorine; and
a second fluoromonomer of the general formula $CF_2CXY$, wherein n is an integer, and wherein X and Y are selected from the group consisting of hydrogen, halogens, unsubstituted hydrocarbyl groups, inertly substituted hydrocarbyl groups and any combination thereof.

16. The copolymer according to claim 15 wherein said copolymer is selected from the group consisting of random, block, alternating, branched and graft copolymers.

17. The copolymer according to claim 16 wherein said copolymer is one of a random and alternating copolymer prepared by a process of free radical bulk polymerization.

18. The copolymer according to claim 17 wherein said copolymer is one of a random and alternating copolymer prepared by a process of redox emulsion polymerization.

19. A copolymer, comprising:
a fluoromonomer of the general formula $CGJ=CL(OCH_2CH_2)_nOR$, wherein n is an integer and R represents an unsubstituted or inertly substituted hydrocarbyl group, G and J are selected from the group consisting of chlorine, fluorine, trifluoromethyl and hydrogen, and wherein L is selected from the group consisting of chlorine, fluorine and hydrogen, and wherein at least one of G, J and L is fluorine; and
a second fluoromonomer of the general formula CFXCYZ, wherein X, Y and Z are selected from the group consisting of hydrogen, halogens, hydrocarbyl groups, inertly substituted hydrocarbyl groups and any combination thereof.

20. The copolymer according to claim 19 wherein said copolymer is selected from the group consisting of random, block, alternating, branched and graft copolymers.

21. The copolymer according to claim 20 wherein said copolymer is one of a random and alternating copolymer prepared by a process of free radical bulk polymerization.

22. The copolymer according to claim 21 wherein said copolymer is one of a random and alternating copolymer prepared by a process of redox emulsion polymerization.

23. A copolymer, comprising:
a fluoromonomer having a general formula $CGJ=CL(OCH_2CH_2)_nOR$, wherein n is an integer and R represents an unsubstituted or inertly substituted hydrocarbyl group, G and J are selected from the group consisting of chlorine, fluorine, trifluoromethyl and hydrogen, and wherein L is selected from the group consisting of chlorine, fluorine and hydrogen, and wherein at least one of G, J and L is fluorine; and
a second monomer having a generic formula CXYCAB, wherein X, Y, A, B are selected from the group consisting of hydrogen, halogen; unsubstituted hydrocarbyl groups, inertly substituted hydrocarbyl groups and any combination thereof.

24. The copolymer according to claim 23 wherein said copolymer is selected from the group consisting of random, block, alternating, branched and graft copolymers.

25. The copolymer according to claim 24 wherein said copolymer is one of a random and alternating copolymer prepared by a process of free radical bulk polymerization.

26. The copolymer according to claim 25 wherein said copolymer is one of a random and alternating copolymer prepared by a process of redox emulsion polymerization.

27. A terpolymer, comprising;
a first fluoromonomer of the following general formula $$CF_2=CF(OCH_2CH_2)_nOR$$

wherein n is an integer greater than or equal to 1 and R represents an unsubstituted or inertly substituted hydrocarbyl group;

a second fluoromonomer of the following general formula $$CF_2=CF(OCH_2CH_2)_nOR'$$

wherein n is an integer greater than or equal to 1 and R' represents an unsubstituted or inertly substituted hydrocarbyl group;

a third fluoromonomer of the following general formula $$CF_2=CF(OCH_2CH_2)_nOR''$$

wherein n is an integer greater than or equal to 1 and R'' represents an unsubstituted or inertly substituted hydrocarbyl group, wherein R, R' and R'' are different from each other.

28. A terpolymer comprising;
a first fluoromonomer of the following general formula $$CF_2=CF(OCH_2CH_2)_nOR$$

wherein n is an integer greater than or equal to 1 and R represents an unsubstituted or inertly substituted hydrocarbyl group;

a second fluoromonomer of the following general formula $$CF_2=CF(OCH_2CH_2)_nOR'$$

wherein n is an integer greater than or equal to 1 and R' represents an unsubstituted or inertly substituted hydrocarbyl group, wherein R and R' are different; and a third fluoromonomer of the general formula $CF_2CXY$, wherein X and Y are selected from the group consisting of hydrogen, halogen, unsubstituted hydrocarbyl groups, inertly substituted hydrocarbyl groups and any combination thereof.

29. A terpolymer comprising;
a first fluoromonomer of the following general formula $$CF_2=CF(OCH_2CH_2)_nOR$$

wherein n is an integer greater than or equal to 1 and R represents an unsubstituted or inertly substituted hydrocarbyl group;

a second fluoromonomer of the general formula $CF_2=CF(OCH_2CH_2)_nOR'$, wherein n is an integer greater than or equal to 1 and R' represents an unsubstituted or inertly substituted hydrocarbyl group, wherein R and R' are different; and a third fluoromonomer of the general formula CFXCYZ, wherein X, Y and Z are selected from the group consisting of hydrogen, halogen, unsubstituted hydrocarbyl and inertly substituted hydrocarbyl groups and any combination thereof.

30. A terpolymer comprising;
a first fluoromonomer of the following general formula $$CF_2=CF(OCH_2CH_2)_nOR$$

wherein n is an integer greater than or equal to 1 and R represents an unsubstituted or inertly substituted hydrocarbyl group;

a second fluoromonomer having a general formula $CF_2=CF(OCH_2CH_2)_nOR'$, wherein n is an integer greater than or equal to 1 and R' represents an unsubstituted or inertly substituted hydrocarbyl group wherein R and R' are different; and a third monomer having a generic formula CXYCAB, wherein X, Y, A, B are selected from the group consisting of hydrogen, halogen, unsubstituted hydrocarbyl groups, inertly substituted hydrocarbyl groups and any combination thereof.

31. A graft copolymer, comprising:
a polymer graft and a polymer backbone, said backbone comprising a polymer selected from the group consisting of polystyrene, polyurethane, polyester, polyether, polyethylene, polypropylene, poly(carbonate), poly(anhydride), poly(vinyl chloride), poly(acrylonitrile), poly(α-hydroxyesters), poly(tetrafluoroethylene), poly(vinylidene fluoride), poly(chlorotrifluoroethylene), nylon, poly(ethylene terephthalate), poly(amide), poly(amine), poly(amino acid), poly(arylate), poly(acrylate), poly(acetate) and any combination thereof; and said polymer graft comprising a fluoropolymer of the following general formula $$-[CF_2CF\{(OCH_2CH_2)_nOR\}]_m-$$

wherein n is an integer, m is an integer and R represents an unsubstituted or inertly substituted hydrocarbyl group.

32. A fluoropolymer blend, comprising:
a fluoropolymer of the following general formula $$-[CF_2CF\{(OCH_2CH_2)_nOR\}]_m-$$

wherein n is an integer, m is an integer and R represents an unsubstituted or inertly substituted hydrocarbyl group, said fluoropolymer having a fluorocarbon backbone; and a polymer selected from the group consisting of polystyrene, polyurethane, polyester, polyether, polyethylene, polypropylene, poly(carbonate), poly(anhydride), poly(vinyl chloride), poly(acrylonitrile), poly(α-hydroxyesters), poly(tetrafluoroethylene), poly(vinylidene fluoride), poly(chlorotrifluoroethylene), nylon, poly(ethylene terephthalate), poly(amide), poly(amine), poly(amino acid), poly(acrylate), poly(acetate) and any combination thereof.

33. Biologically useful materials exhibiting low protein absorption, comprising;
fluoropolymers blended with physiologically acceptable polymer, the fluoropolymers being selected from the group consisting of $-[CF_2CF\{(OCH_2CH_2)_nOR\}]_m-$, wherein n is an integer, m is an integer and R represents an unsubstituted or inertly substituted hydrocarbyl group, said fluoropolymer having a fluorocarbon backbone.

* * * * *